(12) United States Patent
Köhler et al.

(10) Patent No.: US 10,645,372 B2
(45) Date of Patent: May 5, 2020

(54) OBSERVATION DEVICE COMPRISING A CONTROL UNIT

(71) Applicant: Karl Storz GmbH & Co. KG, Tuttlingen (DE)

(72) Inventors: Benedikt Köhler, Wurmlingen (DE); Andreas Heni, Tuttlingen (DE); Markus Kupferschmid, Tuttlingen (DE); Eckhart Baum, Duerbheim (DE); Peter Schwarz, Tuttlingen-Nendingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 547 days.

(21) Appl. No.: 15/367,600

(22) Filed: Dec. 2, 2016

(65) Prior Publication Data
US 2017/0163972 A1 Jun. 8, 2017

(30) Foreign Application Priority Data

Dec. 3, 2015 (DE) .......................... 10 2015 121 017

(51) Int. Cl.
*H04N 13/296* (2018.01)
*H04N 5/232* (2006.01)
(Continued)

(52) U.S. Cl.
CPC ......... *H04N 13/296* (2018.05); *A61B 1/0005* (2013.01); *A61B 1/00009* (2013.01);
(Continued)

(58) Field of Classification Search
CPC .. H04N 13/296; H04N 13/239; A61B 1/0005; G06F 3/0485
See application file for complete search history.

(56) References Cited

U.S. PATENT DOCUMENTS

| 5,223,776 A | 6/1993 | Radke et al. |
| 5,313,306 A | 5/1994 | Kuban et al. |

(Continued)

FOREIGN PATENT DOCUMENTS

| CA | 2605071 C | 4/2013 |
| DE | 69116540 12 | 8/1996 |

(Continued)

OTHER PUBLICATIONS

Baumann, Konrad; Lanz, Herwig: Mensch-Maschine-Schnittstellen elektronischer Gerate. Leiffaden fur Design und Schaltungstechnik. "Human-machine-interfaces of electronic devices. Guideline for design and circuit technology". ISBN 978-3-642-637384. Berlin; Heidelberg: Springer, 1998. Kapitel 2: Bedienelemente, S. 35-79.

(Continued)

*Primary Examiner* — Irfan Habib
(74) *Attorney, Agent, or Firm* — Whitmyer IP Group LLC

(57) ABSTRACT

An observation device is provided with an image acquisition unit comprising at least one image sensor, an image display unit, that is arranged for displaying image data that is provided by the image acquisition unit, an image processing unit for image processing procedures, and a control unit comprising a multi-axis input module. The image acquisition unit is configured to provide recorded images having a predefined recording pixel quantity. The image display unit is configured to display images having a predefined display pixel quantity, wherein the recording pixel quantity is equal to or greater than the display pixel quantity. Image pixels of the display pixel quantity are obtained from the recording pixel quantity. Subsets of the recording pixel quantity are selected to form the display pixel quantity. Image acquisition parameters and display parameters are controlled by the input module. The input module is arranged to be coupled (Continued)

with the image acquisition unit for controlling at least one image acquisition parameter.

19 Claims, 8 Drawing Sheets

(51) Int. Cl.
| | |
|---|---|
| *G06F 3/0484* | (2013.01) |
| *H04N 13/239* | (2018.01) |
| *A61B 1/00* | (2006.01) |
| *G06F 3/0338* | (2013.01) |
| *G06F 3/01* | (2006.01) |
| *G06F 3/0485* | (2013.01) |
| *G06F 3/0362* | (2013.01) |
| *H04N 5/225* | (2006.01) |
| *H04N 5/33* | (2006.01) |
| *H04N 7/18* | (2006.01) |

(52) U.S. Cl.
CPC .......... *A61B 1/00188* (2013.01); *G06F 3/011* (2013.01); *G06F 3/016* (2013.01); *G06F 3/0338* (2013.01); *G06F 3/0362* (2013.01); *G06F 3/0485* (2013.01); *G06F 3/04847* (2013.01); *H04N 5/2256* (2013.01); *H04N 5/232* (2013.01); *H04N 5/23216* (2013.01); *H04N 5/23293* (2013.01); *H04N 5/332* (2013.01); *H04N 13/239* (2018.05); *A61B 1/00147* (2013.01); *G06F 2203/04806* (2013.01); *H04N 7/183* (2013.01); *H04N 2005/2255* (2013.01)

(56) References Cited

U.S. PATENT DOCUMENTS

| | | | |
|---|---|---|---|
| 6,222,906 B1 | 4/2001 | Sakaguchi et al. | |
| 6,429,849 B1 | 8/2002 | An et al. | |
| 7,038,667 B1 | 5/2006 | Vassallo et al. | |
| 8,982,203 B2* | 3/2015 | Berci ................ | A61B 1/00149 |
| | | | 348/74 |
| 9,532,010 B2* | 12/2016 | Baumann ................ | H04N 7/18 |
| 2006/0255683 A1* | 11/2006 | Suzuki .................... | G05G 1/10 |
| | | | 310/317 |
| 2007/0030450 A1* | 2/2007 | Liang ....................... | A61B 3/14 |
| | | | 351/206 |
| 2008/0231692 A1* | 9/2008 | Higuchi ............... | A61B 1/0005 |
| | | | 348/65 |
| 2010/0123782 A1 | 5/2010 | Yata | |
| 2010/0157083 A1 | 6/2010 | Ohya et al. | |
| 2013/0016204 A1 | 1/2013 | Hocke et al. | |
| 2013/0314579 A1 | 11/2013 | Sasaki | |
| 2014/0015954 A1* | 1/2014 | Tsujimoto ................ | G06T 3/40 |
| | | | 348/79 |
| 2014/0063201 A1* | 3/2014 | Ohkoba ............ | A61B 1/00009 |
| | | | 348/48 |
| 2015/0025547 A1 | 1/2015 | Hannaford et al. | |
| 2015/0085084 A1 | 3/2015 | Heni et al. | |
| 2015/0130759 A1 | 5/2015 | Heo | |

FOREIGN PATENT DOCUMENTS

| | | |
|---|---|---|
| DE | 20014425 U1 | 1/2001 |
| DE | 60131839 T2 | 12/2008 |
| DE | 102009037016 A1 | 2/2011 |
| DE | 102011078967 A1 | 1/2013 |
| DE | 102013110543 A1 | 3/2015 |

OTHER PUBLICATIONS

German Search Report and Translation Application No. DE 10 2015 121 017.7 dated Aug. 11, 2016 20 pages.
Handels, Heinz: Medizinische Bildverarbeitung. Bildanalyse, Mustererkennung und Visualisie—rung fur die computergesttitzte arztliche Diagnostik und Therapie. "Medical image processing. Image analysis, pattern detection and visualization for computer-aided medical diagnosis and therapy." 2. Auflage. ISBN 978-3-8351-0077-0. wiesbaden: Vieweg+Teubner / GWV Fachverlage, 2009. Kapitel 9: Visualisierung medi—zinischer Bilddaten, S. 283-344.
Kleti [Publisher]: Google Earth Tutorial. Abschnitt 1.3: Steuerung/Navigation in Google Earth und wichtige Tastaturbefehle; 1.: SteuerunglNavigation mithilfe der Maus. Unterrichtsmateria—lien zu: Planungsprozesse bewerten—Stuttgart 21 ISBN 978-3-12-104119-0. Stuttgart, Leipzig: Ernst Klett Verlag, 2014.
Kramme, Rudiger (Editor): Medizintechnik: Verfahren-Systeme-Informationsverarbeitung. "Medical Technology: Methods-Systems-Information processing" 4. Auflage. ISBN 978-3-642-16186-5. Berlin; Heidelberg; New York: Springer, 2011. Kapitel 21: Endoskopie, S. 379-401.
Lauffs, Hans-Georg: Bediengerate zur 3D-Bewegungsfiihrung. Ein Beitrag zur Ethzienten Robo-terprogrammierung. "Control devices for 3D movement control. A contribution to ethciant robot programming." ISBN 978-3-528-06439-6. Reihe Fortschritte der Robotik, Band 9. Braun-schweig: Friedr. Vieweg & Sohn, 1991. Kapitel 4.: Bedienelemente zur Bewegungsprogrammie-rung, S. 21-30; Kapitel 5.: Bewegungsfuhrung mit Kraftvorgabe, S. 31-37.
European Search Report Patent No. 16202058.0 Completed: Apr. 25, 2017; dated May 9, 2017 7 pages.
European Examination Report. Application No. 16202058.0 Completed: Aug. 8, 2019 7 Pages.

* cited by examiner

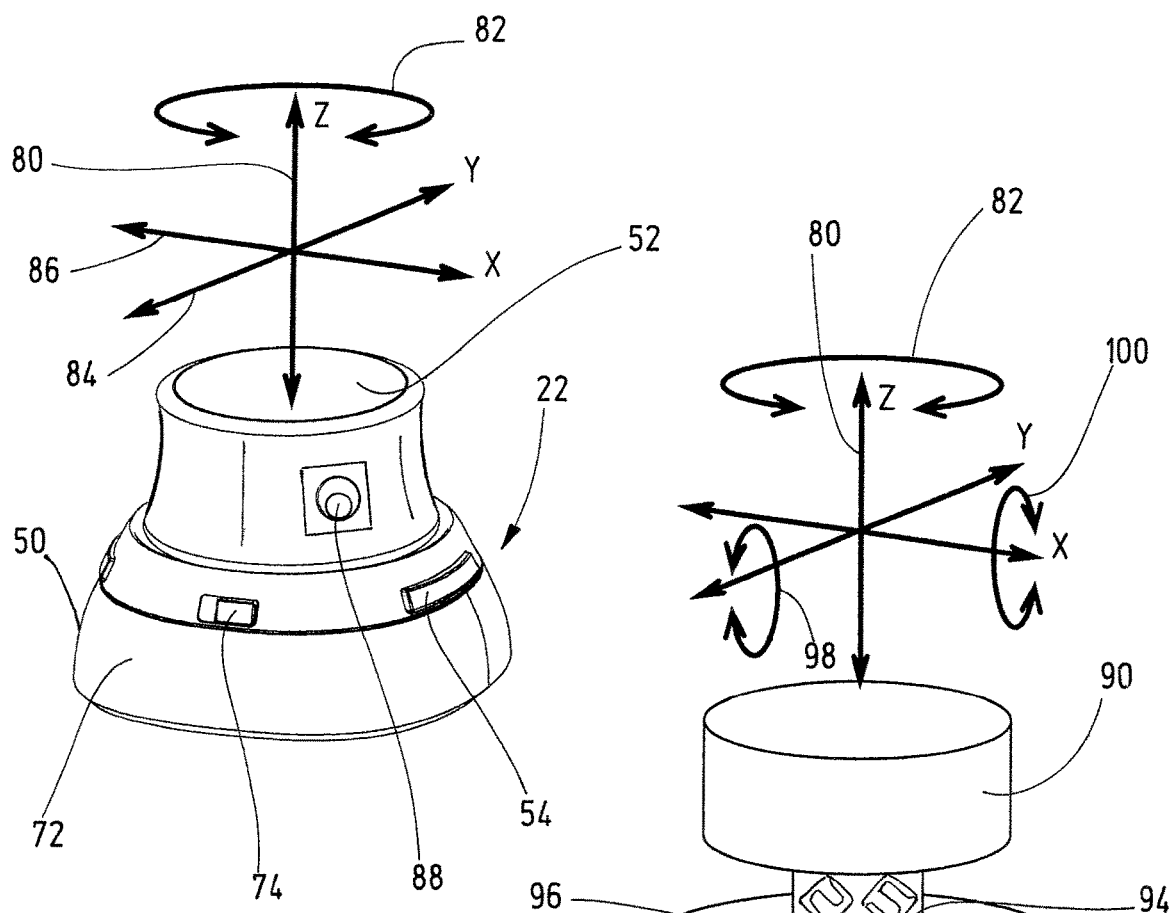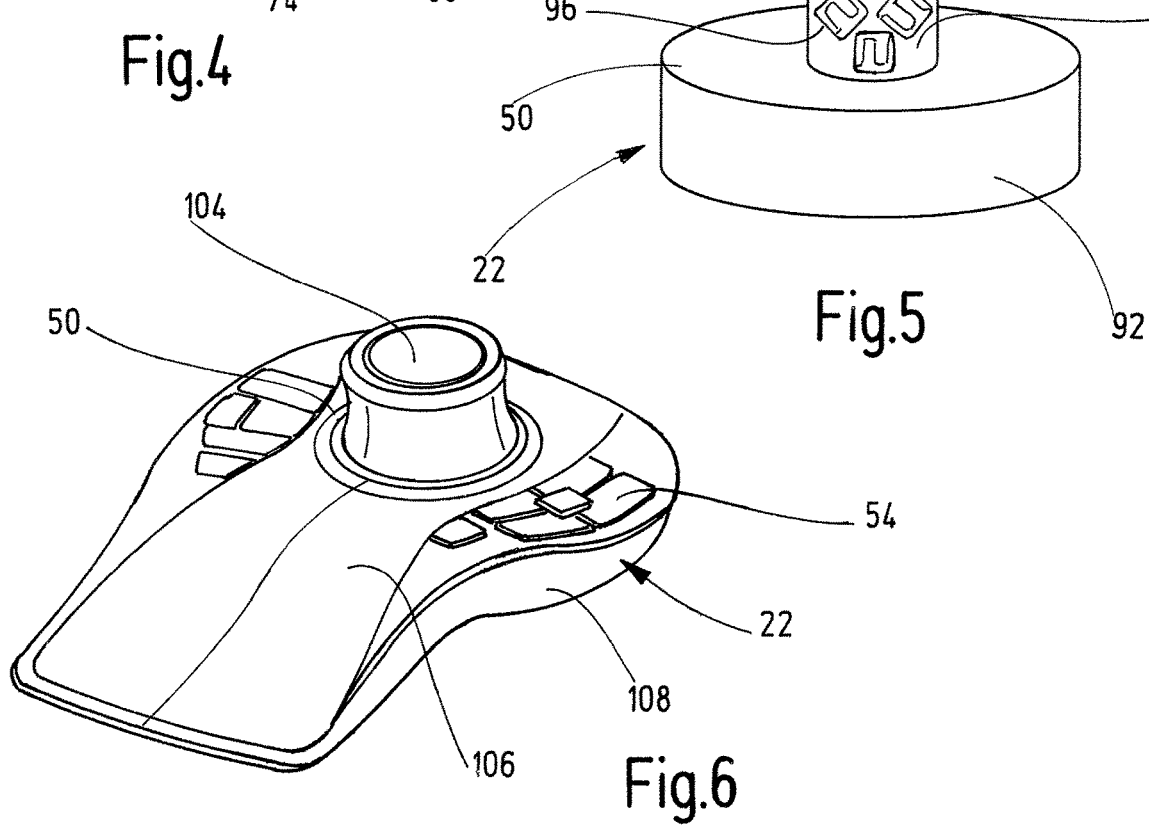
Fig.4
Fig.5
Fig.6

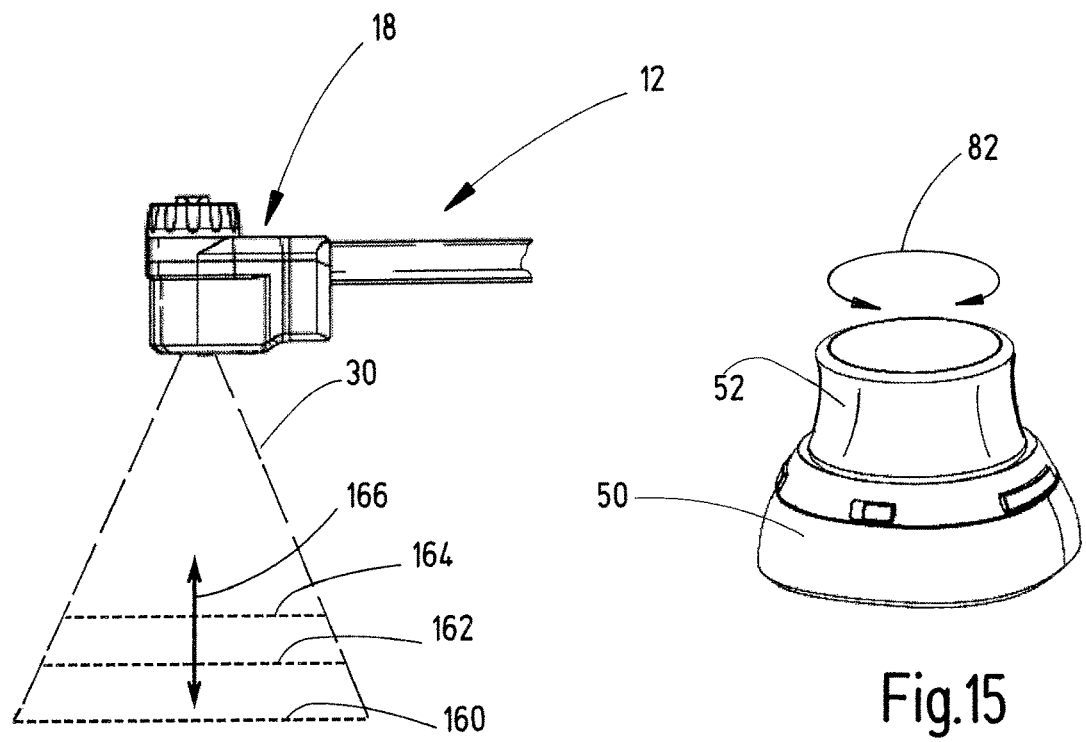
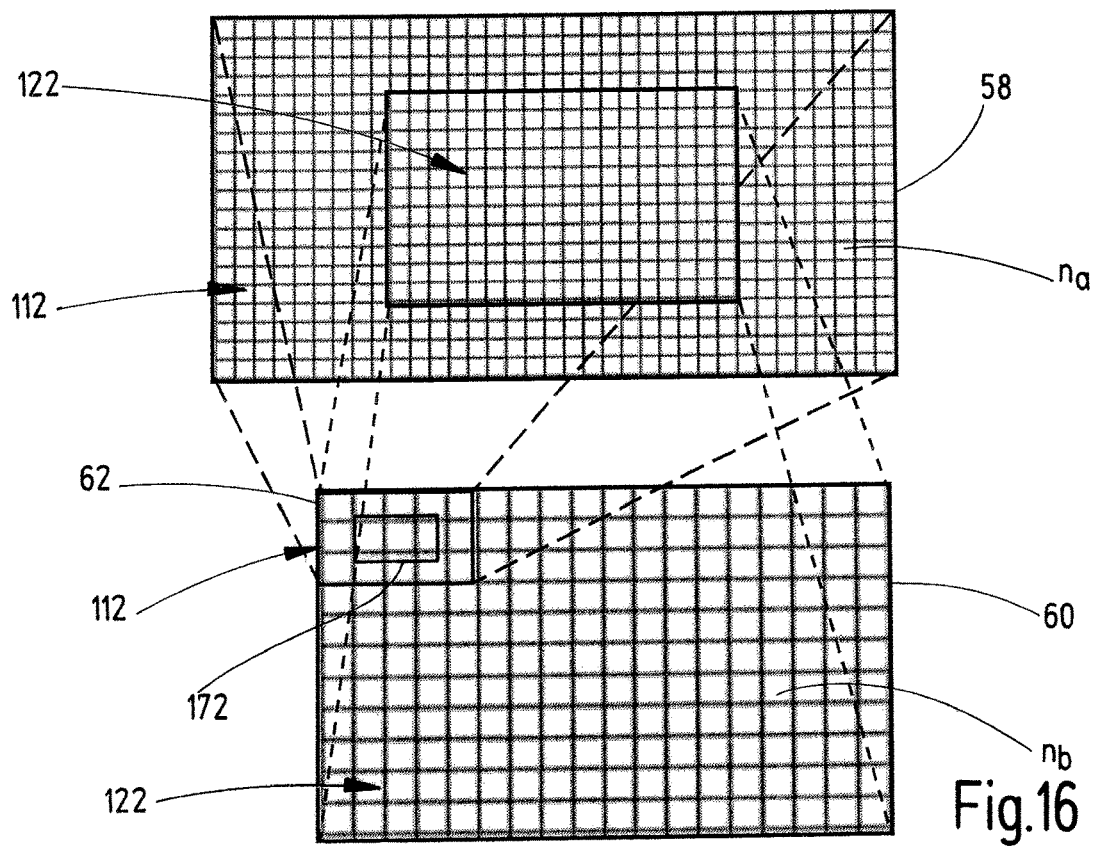
Fig.15
Fig.16

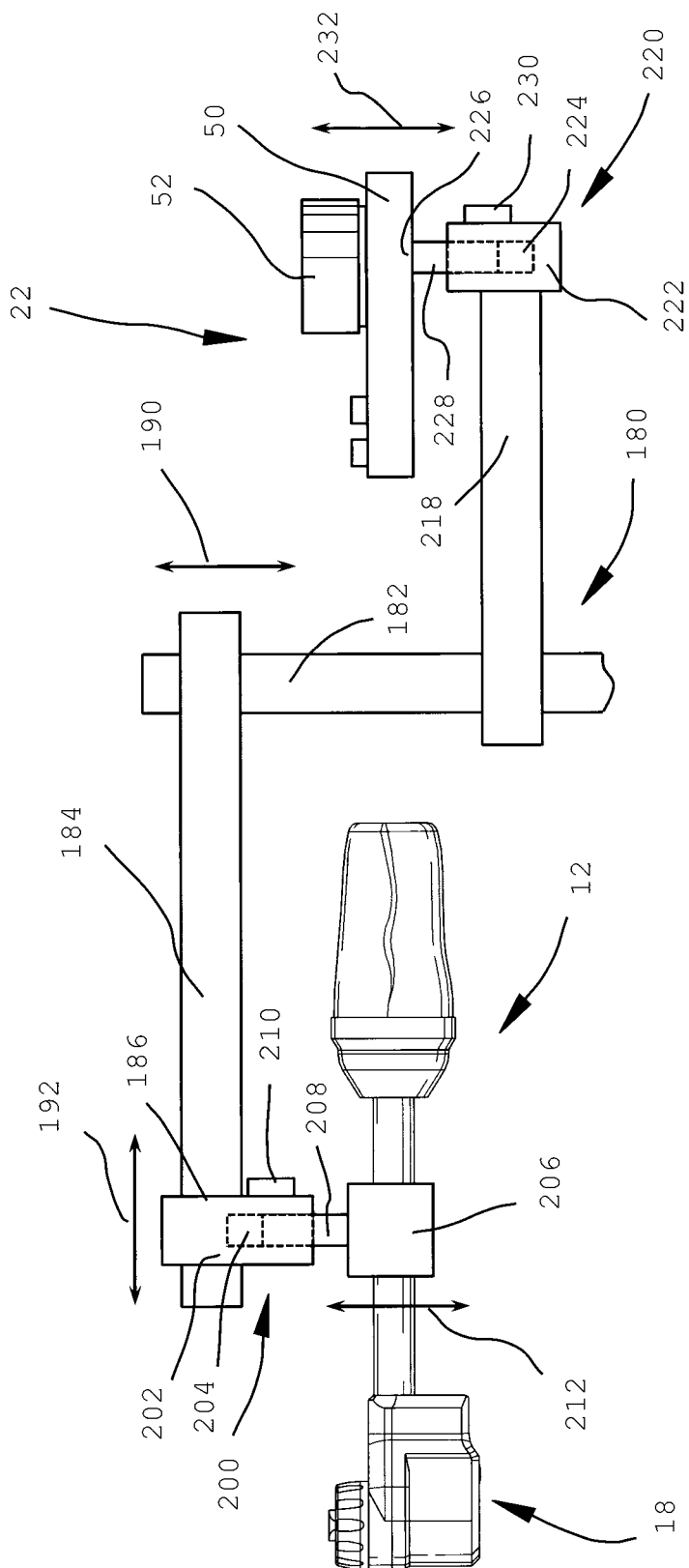
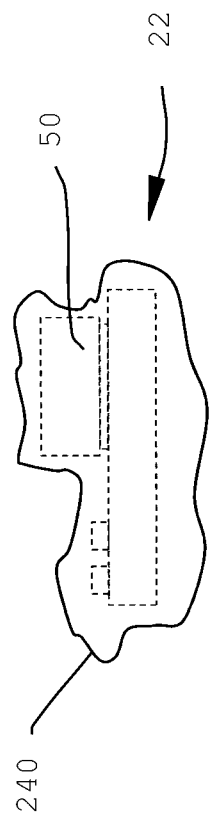
Fig. 17
Fig. 18

OBSERVATION DEVICE COMPRISING A CONTROL UNIT

CROSS-REFERENCES TO RELATED APPLICATIONS

This application claims priority from German patent application 10 2015 121 017.7, filed on Dec. 3, 2015. The entire content of that priority application is fully incorporated by reference herewith.

BACKGROUND

The present disclosure relates to an observation device, particularly to a medical observation device, comprising an image acquisition unit, an image display unit, an image processing unit, and a control unit. The disclosure further relates to a use of a multi-axis input module.

Observation devices in the context of the present disclosure may involve endoscopes, exoscopes and similar optical instruments. This preferably involves optical instruments that are equipped with image sensors to generate a digital image of an object to be observed. Instruments of that kind are regularly arranged as so-called eyepieceless instruments. In other words, instruments of that kind do not exclusively involve a conventional optical beam path between the objective and an eye of a user.

Instead, eyepieceless instruments regularly involve image display units that are formed as screens, video glasses (head-mounted displays) and such like. This may involve several advantages. For instance, a plurality of image display units that can use the same image signal may be easily coupled.

Further, eyepieceless instruments are known that are configured for stereoscopic visualization. Instruments of that kind for instance comprise two image sensors that are disposed adjacent to one another and that comprise a defined offset (distance or offset angle) therebetween.

Image sensors may generally be coupled with appropriate input beam geometrical optics. In this way, desired optical imaging may be achieved.

The present disclosure, at least in some exemplary embodiments, relates to observation devices having compact-shape image acquisition units. Both for endoscopes and for exoscopes, small dimensions are appreciated, for instance at the distal end of the instruments. In endoscopes, this may relate to a cross section or a diameter of the distal end. Endoscopes are regularly arranged to be inserted in body orifices. To keep the stress for patients as low as possible, small dimensions are intended. The distal end of an endoscope generally is referred to as the end that is remote from the user and/or the observer. A proximal end that is opposite to the distal end generally is referred as an end that is close to the user and/or observer An exoscope may generally be referred to as microscope. Exoscopes are regularly arranged to observe a target object from exterior of the body from a defined working distance that may for instance be between 25 to 75 cm (centimeter). However, also for exoscopes it is intended to form image acquisition units, objectives and/or, more generally seen, the distal end (remote from the observer) in a compact fashion. In this way, a preferably not-obstructed viewing field is provided to the operating surgeon. Even when an exoscope is arranged at a defined working distance from an object (for instance an operation site to be observed), the accessibility of the operation site should preferably be extensively ensured.

The desired compactness involves that in eyepieceless endoscopes and exoscopes frequently complex units for adapting the focal length (optical zoom) are dispensed with. However, applications may be foreseen, wherein only a section of a currently detected object field at a given focal length is interesting. Both for endoscopes and also for exoscopes, the working distance often may not be arbitrarily varied. Because of their compactness, optical instruments that are arranged as endoscopes or exoscopes, for instance, are typically manually guided. However, several applications can be foreseen, wherein the instrument is fixedly attached to a stand or a similar mounting device. For instance, this is an option when an image is desired that is preferably blurr-free. Further, the fixation of the instrument may have the effect that for the operating surgeon or an assistant both hands are available for other activities.

In eyepieceless instruments, particularly in eyepieceless exoscopes or endoscopes, it is possible to arrange image sensors very close to an objective of the instruments. As no (optical) eyepiece is provided, it is not required to guide an optical beam path through the instrument and/or through a considerable portion of the instrument. In other words, close to the distal end of the instrument, an image of the object to be observed may be detected and converted into electric signals. Based on the electric signals, image data may be derived. This regularly involves that also at the instrument itself certain data-processing capacity is provided. This may involve at least a limited computing capacity. Further, buffer memories and similar components may be provided.

Further, an eyepieceless instrument generally comprises an interface through which image data may be sent to an image display unit or an (external) image processing unit. Image data may involve so-called raw data. However, image data already may be processed in the instrument itself.

No conventional eyepiece is provided by means of which an observation beam path is directly visible to a human eye (for instance of an operating surgeon). In an eyepieceless instrument in the context of the present disclosure, a conversion and/or transformation of optical signals of the observation field into image data is performed and, in turn, the image data is transferred into optical signals, for instance for the purpose of presentation at a screen.

An exoscope within the general meaning applied in the present disclosure is for instance known from US 2015/0085084 A1. The exoscope disclosed therein is configured as a stereo-exoscope and comprises stereo optics for sensing stereo images.

An observation device arranged as a microscope unit comprising an operation microscope is known from US 2013/0016204 A1. The microscope device further comprises a screen on which invocable device functions are displayable. For selecting and for activating the displayed device functions, a so-called rotary-push control element is provided. The rotary-push control element comprises two actuation axes, namely a rotation axis for rotation actuation, and a translational axis for a push actuation.

In view of this, it is an object of the present disclosure to present an observation device that is arranged to be operable in a simple and low error fashion and that enables a compact-shaped design of at least an image acquisition unit of the observation device.

It is a further object of the present disclosure to present a respective medical observation device.

It is a further object of the present disclosure to present an observation device nevertheless provides extended functions, for instance the option to select and modify a magnification of the image of the object field.

It is a further object of the present disclosure to present an observation device having a control unit that is operatively coupled with the observation device in such a way that an intuitive control of at least part-functions relating to the detection and part-functions relating to image displaying is enabled.

It is a further object of the present disclosure to present an observation device comprising a control unit having a control logic wherein an operator, without doing it intentionally, may easily control recorded images that are provided by the image acquisition unit and display images that are provided by the image display unit.

It is a further object of the present disclosure to present an observation device comprising a control unit wherein, at first, for instance, it is of no significance from the operators point of view whether he/she directly controls an optics of the image acquisition unit, or controls signal processing and/or data processing relating to the recorded images by an actuation of the control unit.

It is a further object of the present disclosure to present an observation device comprising a control unit that enables an interconnection of the image acquisition unit with the image processing unit and the image display unit, at least in terms of control, wherein the interconnection operationally couples part-systems with one another and, so to say, enables a consistent/integral control of the coupled system.

It is a further object of the present disclosure to present beneficial uses of an input module in a control unit for an observation device. This may involve that the input module, in the operators view, enables an interconnection of part-systems of the observation device, so that the operator, using merely one input module, may control the image acquisition unit, the image display unit and the image processing unit in unison.

SUMMARY

In regard of the observation device, these and other objects are achieved by an observation device comprising:

an image acquisition unit comprising at least one image sensor, preferably a stereo-image acquisition unit comprising two image sensors, an image display unit that is arranged to display image data that is provided by the image acquisition unit, an image processing unit for image processing procedures, and a control unit comprising a multi-axis input module, wherein the control unit is configured to provide recorded images having a predefined recording pixel quantity, wherein the image display unit is configured to display images having a predefined display pixel quantity, wherein the recording pixel quantity is equal to or greater than the display pixel quantity, wherein image pixels of the display pixel quantity are obtainable from the recording pixel quantity, wherein, for providing views having different magnifications, subsets of the recording pixel quantity are selectable to form the display pixel quantity, wherein image acquisition parameters and display parameters are controllable by the input module, and wherein the input module is arranged to be coupled with the image acquisition unit for controlling at least one image acquisition parameter.

The above aspect is based on the insight that, at least in some exemplary embodiments of the present disclosure, the multi-axis input module of the control unit enables a simple, integrated control of the observation device. At first, it is of no significance whether an operator (for instance an operating surgeon or an assistant) controls by means of an actual input the image acquisition unit, the image processing unit or the image display unit. As the input module is arranged as a multi-axis input module, the image acquisition unit, the image display unit and/or the image processing unit may be simultaneously or nearly simultaneously controlled. The result of such an input is immediately visible to the operator due to a change of the displayed image. It is of no significance whether the change of the displayed image is induced by influencing the image acquisition unit, the image processing unit or the image display unit. The interconnection between the input module and the image acquisition unit may take place in mediate or immediate fashion. The interconnection between the input module and the image acquisition unit is functional or structural.

The display parameter may be for instance a currently selected magnification (zoom factor). The display parameter may further relate to a current position of a displayed image in a provided global recorded image. To control display parameters of that kind, the input module may mediately or immediately control the image processing unit and/or image display unit. The image acquisition parameter may for instance relate to a current position and/or a current distance of a focus plane or generally a focus parameter. For instance, the image acquisition unit is provided with a focus drive. Accordingly, the input module may be mediately or immediately coupled with the image acquisition unit to control the focus drive. The image acquisition parameter may, however, further relate to an illumination of the currently observed object field. The image acquisition parameter may further relate to an activation of filters, apertures, mirrors and such like.

In certain embodiments, the observation device is a medical observation device. In certain embodiments, the at least one sensor is arranged to detect incident electromagnetic radiation in at least one of an UV range, a visible light range, and a (N)IR range. As used herein, image capturing involves detecting electromagnetic radiation that has substantially been reflected by an object to be observed, e.g. by a body part or an organ of a patient.

The at least one sensor may be arranged to detect light in at least one section of a wavelength range between about 10 nm (nanometers) to about 1.400 nm. As used herein, ultraviolet light (UV) is an electromagnetic radiation with a wavelength from about 10 nm to about 400 nm. As used herein, visible light is an electromagnetic radiation with a wavelength from about 400 nm to about 700 nm. Near-infrared light (NIR) is an electromagnetic radiation with a wavelength from about 700 nm to about 1.400 nm.

In certain embodiments, the acquisition unit is a stereo-image acquisition unit comprises two image sensors for stereoscopic imaging.

In an exemplary embodiment, the input module is further arranged to be coupled with the image acquisition unit to control at least one display parameter. Hence, in accordance with this embodiment, image processing already takes place, at least partially, at the optical instrument itself and/or at the image acquisition unit thereof. The display parameter for instance relates to an image scale (magnification factor and/or zoom factor). If a desired image scale or image section may be generated by a targeted selection of defined sets or subsets of the recording pixel quantity, also the image acquisition unit itself may be used for image processing to meet with desired display parameters. Similarly, also an image position may be changed when a section of the recording pixel quantity is shifted and/or re-positioned within the area that is provided by the recording pixel quantity.

In other words, in accordance with this embodiment, the optical instrument itself and/or the image acquisition unit thereof are, at least to some extent, configured for image processing. This may involve providing views having different magnifications and a digital "shifting" of an image section. This measure has the effect that the data amount that is exchanged between the image acquisition unit and an external image processing unit and/or image display unit is reduced. This may accelerate image processing procedures and the provision and/or presentation of the desired image data.

Hence, a (part-) image processing unit of the image acquisition unit may be associated with the image acquisition unit and/or the optical instrument. In accordance with this embodiment, image processing may be regarded as a distributed task, namely partially in an internal (part-) image processing unit and an external (part-) image processing unit—in each case in the view of the instrument. The internal (part-) image processing unit may be a part module of the image acquisition unit. It may also be envisaged to provide a separate internal (part-) image processing unit at the instrument in addition to the image acquisition unit.

The image acquisition unit of the observation device is, in certain embodiments, arranged as eyepieceless image acquisition unit. In other words, no exclusively optical observation beam path is provided to the operator. Instead, for instance recording optics is provided, wherein the at least one image sensor is coupled to the "ocular" of the recording optics. In certain embodiments, the image acquisition unit does not comprise an optical zoom. In this way, the image acquisition unit may be arranged in a considerably compact-design fashion. For instance, the image acquisition unit may be arranged as a part of an optical instrument, for instance an exoscope or endoscope. In certain embodiments, the image acquisition unit is arranged at the distal end of the optical instrument. Further, the image acquisition unit is for instance provided with or coupled to an illumination module.

In certain embodiments, the display unit is configured for immediately displaying (instant or quasi-instant displaying) recorded images. In certain embodiments, the image acquisition unit is arranged as stereo-image acquisition unit. Accordingly, also the image display unit is then equipped for visualizing stereoscopic images. To this end, the image display unit may be configured for visualizing two (stereo-) channels. An observer or operator may spatially perceive the image provided by the image display unit, using suitable means (3D-glasses and such like). Further variations may be envisaged, for instance providing autostereoscopic screens. It is understood that in addition to the stereoscopic visualization also a (volumetric) 3D-visualization may generally be envisaged.

However, the present disclosure does not relate to a reproduction of models, but to an immediate reproduction (live-reproduction) of an observed object field. As used herein, immediate reproduction involves that an observed scene can be displayed without a temporal delay (lag) that is noticeable by the user (operating surgeon, etc.).

The image processing unit may generally be arranged as central unit. However, in accordance with at least some exemplary embodiments, the image processing unit is arranged as a distributed image processing unit. In other words, the image processing unit may involve modules at least one of which is coupled with and/or provided in the image acquisition unit. In other words, the optical instrument that is provided with the image acquisition unit may be arranged for processing captured (raw) image data. It may therefore be envisaged that the at least one image sensor provides a continuous or quasi-continuous recorded image data stream, wherein already in the optical instrument a selection and/or derivation of a display image data stream or at least of a stream of preprocessed image data takes place. This has the effect that no complex (separate) computing equipment has to be provided between the image acquisition unit and the image display unit. Nevertheless, it may be of course also envisaged that respective image processing modules are provided that are not directly associated with the image acquisition unit. Image processing modules of that kind may be associated with the image display unit. However, it may also be envisaged to provide separate image processing modules that are associated with a computer.

In certain embodiments, the multi-axis input module is arranged to the mediately or immediately coupled with both the image acquisition unit and with the image display unit and/or the image processing unit to control several components of the observation device. To this end, it is not necessary to provide separate control modules for the image acquisition unit, the image display unit and, as the case may be, even for the image processing unit to control the desired functions.

The afore-mentioned components may be coupled to one another via discrete lines. It may however be also envisaged that a common bus line is used. Further types of communication and/or a network topology between the components may be envisaged. It goes without saying that at least some of the components may also communicate with one another in a wireless fashion.

In certain embodiments, the display pixel quantity corresponds to a native resolution of a display of the image display unit. When the image acquisition unit is provided with an image sensor that comprises a great number of single sensors so that overall a recording pixel quantity is present that is greater than the display pixel quantity, a magnification may easily be provided when, in the event of an enlarged view of a partial section of a recorded image, each neighboring pixel of the section is read out. A (reduced-scale) overview may however be used when not each neighboring pixel but for instance each second or each fourth neighboring pixel is used to derive the display image from the recorded image. It goes without saying that intermediate stages may be envisaged. For instance, an image sensor may be used that provides a 4K resolution (4096×2160 pixels) or a similar resolution, wherein the visualization involves a HD resolution (for instance Full HD 1920×1080 pixels or HD ready 1280×720 pixels).

According to an exemplary embodiment of the observation device, the input module is coupled with the image acquisition unit and the image processing unit, to operate the image acquisition unit for modifying image acquisition parameters, and to operate the image processing unit for modifying display parameters. In certain embodiments, the input module is operable in at least a first operation mode and a second operation mode, wherein in the first operation mode a direct control of image acquisition parameters and display parameters is enabled, and wherein in the second operation mode a control of peripheral functions is enabled. The interconnection may be provided in a mediate or immediate fashion. A further unit may be arranged between the image acquisition unit and the image processing unit.

In this way, further peripheral functions can be controlled by means of the input module. This may for instance involve a menu control and such like. For instance, the input module may be used to influence a rotation orientation (image orientation). Accordingly, the input module may operate an actuator that is associated with the image acquisition unit and that is arranged to rotate the at least one image sensor about an axis that is perpendicular to the image sensor surface.

According to an exemplary embodiment of the observation device, there is further provided a positioning drive for the image acquisition unit, wherein the input module, in the second operation mode, is operable to control the positioning drive for positioning the image acquisition unit. To this end, the image acquisition unit may be mounted to a stand, column, or a rack-like structure involving at least one powered positioning axis. As the input module is, in some exemplary embodiments, a multi-axis input module, one and the same element may be actuated to control two, three, or even more powered axes of the positioning drive.

According to a further exemplary embodiment of the observation device, the input module is arranged as single-hand input module, wherein the input module comprises an actuation element that is manipulable by an operator, wherein the actuation element provides a plurality of degrees of freedom of movement for inputs, for instance at least one translational direction, at least one rotation direction and at least two further degrees of freedom and/or movement directions that are arranged as sliding directions or swivel directions. The single-hand input module may be operated using only one hand. Hence, it is ensured that at least a second hand of the operator is available.

In certain embodiments, the input module does not only comprise two degrees of freedom in the form of a rotation direction for rotation and a translational direction for a push movement. In certain embodiments, at least two further degrees of freedom are available that are for instance oriented perpendicular to one another and perpendicular to the translational direction.

According to a further exemplary embodiment of the observation device, the actuation element is puck-shaped or knob-shaped, wherein the actuation element is coupled with sensors to detect a pull/push movement along a longitudinal axis of the actuation element, a rotation about the longitudinal axis, and sliding movements in a plane that is oriented perpendicular to the longitudinal direction, or swivel movements about pivot axes that are oriented perpendicular to the longitudinal axis. In certain embodiments, the actuation element provides a hand rest and/or palm rest. Hence, the operator may simply put down his/her hand on the actuation element and may at least sectionally encompass the same with his/her fingers. It goes without saying that embodiments of the actuation element may be envisaged, wherein the operator engages the actuation element only with his/her fingers without resting the palm thereon.

According to a further exemplary embodiment of the observation device, the actuation element is coupled with at least one sensor that is configured as displacement transducer or force transducer. In certain embodiments, the actuation element is coupled with a plurality of sensors for a multi-axial detection of deformations or movements.

Several types of sensors may be envisaged. This may for instance involve optical sensors that may detect movements of the actuation element. In this context, for illustrative purposes, reference is made to optical sensors of computer mouses.

It may be however also envisaged to design the actuation element as such not in a movable fashion. Instead, sensors may be provided that may detect (minimum) deformations of the actuation element. In other words, the operator may manipulate the actuation element, for instance by compressing, pulling, twisting and/or bending, wherein the deformations resulting therefrom may be detected by appropriate sensors. To this end, strain gages or similar sensors may be provided, for instance.

In certain embodiments, two, three or more sensors are used to provide a respective number of degrees of freedom of movement and/or to detect and discriminate a corresponding number of defined actuations. It goes without saying that the sensors may be arranged to simultaneously detect a plurality of movements (combined actuation movements). This may for instance involve a simultaneous pulling or pushing in combination with a rotation of the actuation element. In this way, using only a single actuation element, further functions may be controlled.

In addition to the actuation element, the input module may comprise further input element, for instance buttons, switches, scroll wheels and such like. In certain embodiments, the actuation element itself is not provided with further input elements. Those may rather be arranged in the surroundings of the actuation element. Hence, the actuation element may be actuated "blind" without the necessity of a visual contact. However, in some exemplary embodiments, it may be envisaged that actuation buttons or actuation switches directly at the actuation element for confirming operator inputs are present.

According to a further exemplary embodiment of the observation device, the actuation element is arranged as four-axis actuation element, wherein an actuation of the first actuation axis defines a magnification and a size of an area of the display image in the recorded image that is associated with the magnification, wherein an actuation of the second actuation axis defines a focus setting, wherein an actuation of the third actuation axis causes a movement of the area that is covered by the display image in an area that is covered by the recorded image in a first movement direction, and wherein an actuation of the fourth actuation axis causes a movement of the area that is covered by the display images in the area that is covered by the recorded images in a second movement direction that is inclined with respect to the first movement direction. Accordingly, the actuation element comprises four (movement) degrees of freedom to which the actuation axes are assigned.

In certain embodiments, the first movement direction and the second movement direction are oriented perpendicular to one another.

The focus setting may for instance induce a modification or adjustment of a focus plane. Generally, to this end, optical components of the image acquisition unit are moved. The image acquisition unit may then comprise a focus drive. Further, the focus setting may relate to a variation of a depth of field. The actuation of the first actuation axis, for instance by pushing or pulling, involves a (digital) magnification and/or reduction of the image section that is displayed by the image display unit. An actuation of the third and/or the fourth actuation axis involves a movement of the image section that is currently displayed in a provided image plane. It goes without saying that such a movement is not possible when the area that is currently displayed by the image display unit equals the area that is provided by the image acquisition unit.

The area that is covered by the display images may also be referred to as display area. The area that is provided by the recorded images may also be referred to as recording area.

According to an exemplary refinement the first actuation axis provides a translational direction, wherein the second actuation axis provides a rotation direction having an axis that is parallel to the translational direction, and wherein the third actuation axis and the fourth actuation axis respectively provide a sliding direction, for detecting a lateral deflection perpendicular to the translational direction, or a swivel direction, for detecting a lateral inclination about axes that are oriented perpendicular to the translational axis. It goes without saying that also a combination of a swivel direction and a sliding direction may be envisaged.

In this way, a plurality of functions may be controlled by merely one actuation element that is operable by a single hand.

According to a further exemplary embodiment of the observation device, the recording pixel quantity is an integer multiple of the display pixel quantity, wherein the recording pixel quantity is preferably four times, further preferred eight times the display pixel quantity. By way of example, the display pixel quantity is 1280×720 (HD), preferably 1920×1080 (Full HD). Accordingly, the recording pixel quantity may amount to two times, four times or even eight times of those values. In certain embodiments, an aspect ratio (for instance 16:9 or 4:3) is maintained.

According to a further exemplary embodiment of the observation device, the image processing unit is configured to supply the image display unit with a display pixel quantity that is arranged to be displayed interpolation-free. In certain embodiments, this involves a definition of the display pixel quantity, wherein each display pixel corresponds to a pixel of the recording pixel quantity or to a defined average of a set of pixels (for instance 2×2 or 4×4) of the recording pixel quantity. In other words, in at least some magnification degrees, the observation device enables a loss-free or quasi-loss-free digital zoom. It goes without saying that also intermediate stages may be envisaged, wherein an interpolation is required. It also goes without saying that in the event of a great magnification the to-be-magnified section of the recording area may comprise fewer pixels than the display area, so that then an "upscaling" to the format of the display area is performed. Hence, at least some magnification degrees may involve a lossy digital zoom.

However, this embodiment enables an omission of a complex optical zoom at the image acquisition unit. The digital zoom has the further effect that also when modifying the magnification and/or the image section that is currently displayed by the image display unit, the illumination conditions and the contrast characteristics of the overall image are kept constant. This again results in simplifications on the part of the image acquisition unit.

According to a further exemplary embodiment of the observation device, the image acquisition unit is configured to detect image data of a raw data pixel quantity that is greater than the recording pixel quantity, wherein the raw data pixel quantity corresponds to an overall acquisition range of the image sensor, and wherein the recording pixel quantity is a selected section of the raw data pixel quantity. This arrangement has the effect that a boundary region of the overall acquisition range does not necessarily have to be selected for the provision of the recording area. In the boundary region of image sensors, often adverse optical effects are present, for instance distortions, contrast variations, blurs and such like. It is insofar beneficial that a further processing of the area involved is omitted.

A further benefit of the above-mentioned arrangement may be present when using an image acquisition unit that is configured for stereo detection and that provides two respective image sensors. When the overall acquisition range of at least one of the two image sensors is greater than the area that is respectively selected as recording area, a lateral distance between the both half images that eventually form the stereo image may be modified. This may be used for stereoscopic visualization. For modifying the offset between the half images, no mechanical or optical manipulation is necessary. Rather, the respective recording area may be displaced accordingly in the overall acquisition range.

According to a further exemplary embodiment of the observation device, the control unit is configured to provide haptic feedback at the input module, for instance when reaching limit values or extreme values of parameter ranges that are controllable by the input module.

In this way, the input module for instance may comprise a so-called force feedback function. It may be envisaged to provide vibration generators or similar actuators at the input module, and to couple the same with the actuation element, for instance. The haptic feedback has the effect that the feedback may take place by the tactile perception of the operator, namely directly at the hand by means of which the operator actuates the input module. In this way, no considerable optical and/or acoustical distraction is present.

By way of example, the haptic feedback may be used to signal to the operator that a maximum zoom stage has been reached. A further example for the haptic feedback involves entering a boundary region of the recording area when "displacing" the display areas in the recording area.

According to a further exemplary embodiment of the observation device, the image processing unit is configured to generate overview images that represent an area that basically corresponds to an area that is covered by the recording pixel quantity, wherein the overview images comprise an overview pixel quantity that is selected to be smaller than the display pixel quantity, wherein the overview images are displayable by the image display unit, at least temporarily parallel to the display images, and wherein the overview images at least sectionally overlay the display images. In this way, for instance a picture-in-picture function may be provided. Hence, visual navigation may be simplified. The overview images may be arranged to be semi-transparent. It goes without saying that the overview images do not have to be constantly shown. It may be envisaged to show the overview images when the operator actually operates the input module. This may for instance relate to a displacement of the display area or a modification of the magnification. It is beneficial in these cases to show the overview image.

It goes without saying that separate input elements may be formed at the input module, for instance buttons, switches and such like to show or fade out the overview image on demand.

According to a refinement of the above mentioned embodiment, the image display unit is configured to highlight a section area in the displayed overview image that indicates an area that is covered by the display pixel quantity within the recording pixel quantity, wherein the section area is moved in the overview images when the area that is covered by the display pixel quantity is moved in the area that is covered by the recording pixel quantity, due to an actuation of the control element. In this way, positioning may be even further simplified.

According to a further exemplary embodiment of the observation device, at least the image acquisition unit and the input module of the control unit are autoclavable. In this way, a sterilization of these components may easily take place. This is for instance in the context of medical operations a substantial benefit.

In regard of the input module, it is provided in at least some exemplary embodiments that the detection of the actuation movements takes place by a detection of deformations of the actuation element. Accordingly, the input module that is provided with the actuation element may be integrally shaped and for instance provided with only a small number of distinct components that are movable with respect to one another. In this way, the input module is robust and suitable for several sterilization procedures, for instance.

A further exemplary embodiment and/or operation mode of the observation device involves an assignment of an action, for instance of a function to be controlled, to a plurality of degrees of freedom and/or actuation axes of the actuation element. For instance, a zoom-function may be controlled both by a rotation (using the rotation direction) and by a pull/push movement (using the translational direction). In this way, a redundant operation is enabled. It may be envisaged to assign the assigned degrees of freedom in consideration of a defined hierarchy or priority to the functions so that the operation still may be performed in an unambiguously and intuitive fashion. This may for instance relate to a temporary change of the assignment. It may be further envisaged to effect in this way a coarse adjustment and a fine adjustment, wherein a degree of freedom is assigned to the coarse adjustment and another degree of freedom is assigned to the fine adjustment. This may for instance relate to the zoom-function or the focus drive. Generally, the different degrees of freedom may be different from one another in terms of the sensitivity of the adjustment/actuation.

A further exemplary embodiment and/or operation mode of the observation device involves the definition of preferred functions, wherein accordingly assigned actuations are detected and assessed with high priority. Low priority (subordinate) actuations that may be assigned to functions that are not preferred functions may here be ignored. In other words, defined functions may be blocked so that actuations that are applied via the respective degrees of freedom do not result in respective activities. This may simplify defined actions as undesired actuations of other functions may be avoided. For instance, in some operation modes, a safe decoupling of the zoom-function from the focus drive and/or from a displacement of the image section may take place.

According to a further exemplary embodiment of the observation device, the control unit is provided with a mounting feature comprising a quick release coupling for releasably mounting the control unit to a holder or stand.

According to a further exemplary embodiment of the observation device, the control unit is arranged to be covered with a sterile cover, wherein the input module is arranged to be actuated through the sterile cover.

Further, a similar quick release coupling between the image acquisition unit and the stand may be provided. Preferably, the image acquisition unit and the control unit use the same or similar mounting features for a releasable attachment or mounting to a holder or stand. The image acquisition unit and the control unit can be attached to the same holding system.

In regard of the use, these and other objects are achieved by a use of a multi-axis input module, for instance a single-hand operable input module, in a control unit of a medical observation device for controlling image acquisition parameters and display parameters, wherein the observation device comprises an image acquisition unit for providing recorded images of a predefined recording pixel quantity and an image display unit for displaying display images of a predefined display pixel quantity, wherein the input module comprises plurality of actuation axes, wherein one actuation axis is arranged to be used for selecting a magnification mode, and at least two actuation axes are arranged to be used for moving an area that corresponds to the display image quantity, in consideration of a current magnification mode, in an area that corresponds to the recording pixel quantity.

Also in this way the object of the invention is perfectly achieved.

In certain embodiments, the observation device is refined in accordance with at least one of the aspects described herein. In certain embodiments, the input module is arranged in accordance with at least one of the aspects mentioned herein.

It is to be understood that the previously mentioned features and the features mentioned in the following may not only be used in a certain combination, but also in other combinations or as isolated features without leaving the spirit and scope of the present disclosure.

BRIEF DESCRIPTION OF THE DRAWINGS

Further features and advantages of the disclosure are disclosed by the following description of a plurality of exemplary embodiments, with reference to the drawings, wherein:

FIG. 4 is a perspective top view of an arrangement of a single-hand input module;

FIG. 5 is a perspective top view of a further arrangement of a single-hand input module;

FIG. 6 is a perspective view of yet a further arrangement of a single-hand input module;

FIG. 15 is a schematic simplified view of an input module and an image acquisition unit for elucidating a focus setting;

FIG. 16 is a further schematic comparison of a recorded image and a display image for elucidating a picture-in-picture function;

FIG. 17 is a schematic lateral view of a further embodiment of an observation device; and FIG. 18 is a schematic lateral view of an arrangement of a single-hand input module that is covered with a sterile cover.

DETAILED DESCRIPTION OF EXEMPLARY EMBODIMENTS

Figure 1:
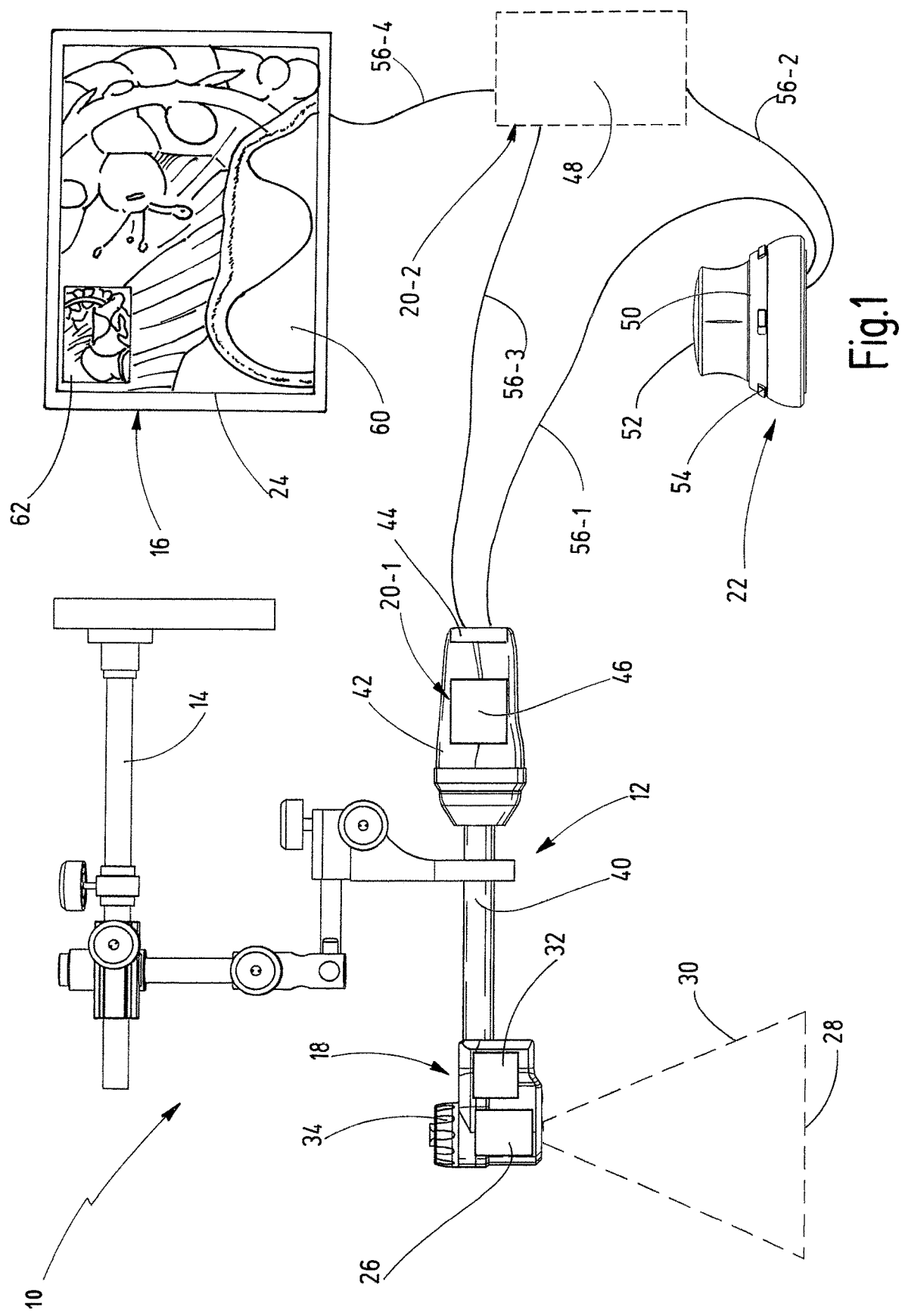
FIG. 1 is a schematic lateral view of an embodiment of an observation device.

FIG. 1 schematically illustrates an exemplary configuration of an observation device 10 that is arranged in accordance with at least some aspects of the present disclosure. The observation device 10 comprises an optical instrument 12. By way of example, the optical instrument is arranged as an exoscope. Alternative embodiments may be envisaged, wherein the optical instrument is arranged as endoscope. The optical instrument 12 is illustratively mounted to a stand 14 which may also be referred to as mounting arm. Accordingly, a fixed orientation of the optical instrument 12 with respect to an object to be observed, for instance a body part or an organ of a patient, is present.

The observation device 10 further comprises an image display unit 16 involving at least one display and/or one screen 24. Both the optical instrument 12 and the image display unit 16 may be arranged as stereoscopic devices. Accordingly, the optical instrument 12 may be arranged to capture right and left half images, wherein the image display unit 16 is configured to display the right and left half images in a desired fashion to generate a stereoscopic (spatial) impression for an observer. Generally, each half image comprises a complete representation of the observed object, wherein an offset or an offset angle may be present between the representations of the right and left half images. In this way, the spatial impression may be generated. The image display unit 16 may further comprise so-called 3D glasses, HMD glasses (head-mounted display) and similar devices.

The optical instrument 12 comprises an image acquisition unit 18. For instance, the image acquisition unit 18 is integrated in the optical instrument 12 and preferably arranged at the distal end thereof. The observation device 10 further comprises an image processing unit 20. The image processing unit 20 may generally be arranged as a centralized image processing unit or a decentralized (distributed) image processing unit. By way of example, FIG. 1 illustrates an arrangement, wherein the image processing unit 20 comprises sections 20-1 and 20-2. The (part) image processing unit 20-1 is associated with the optical instrument 12. The (part) image processing unit 20-2 is, for instance, shown in a separated state and arranged herein as a separate component. It goes without saying that the (part) image processing unit 20-2 may also be at least partially integrated in the image display unit 16 (at least in a structural sense).

Generally, the image processing unit 20 is interposed between the image acquisition unit 18 and the image display unit 16 to process and prepare image data that is provided by the image acquisition unit 18 to supply the data to the image display unit 16 for visualization.

The image acquisition unit 18 comprises at least one image sensor 26 that is arranged to observe a defined object plane 28 and to convert the detected optical signals in electrical (data) signals. A second image sensor (not explicitly shown FIG. 1) enables a stereoscopic imaging. A field of view of the image sensor 26 is indicated in FIG. 1 by 30. The object plane 28 of the optical instrument 12 that is illustratively arranged as an exoscope is in accordance with FIG. 1 spaced away from the image sensor 26, for instance from an objective of the image sensor 26. An exoscope is generally used at an object distance (working distance) in the range of about 250 mm to about 750 mm. The image sensor 26 comprises a CCD sensor, for instance.

The optical instrument 12 shown in FIG. 1 is not configured to be inserted in body orifices and/or further narrow passages. However, the observation device 10 according to alternative arrangements comprises an instrument 12 that is arranged as an endoscopic instrument and that is configured to be inserted in body orifices.

The image acquisition unit 18 further comprises an illumination unit 32. The illumination unit 32 may be integrated in the instrument 12. It may be however also envisaged to couple external light sources to the instrument 12 to provide an illumination for the object plane 28 in the region of the image acquisition unit 18.

Further, an erecting unit or image erection 34 is associated with the image acquisition unit 18. The image erection 34 involves, for instance, a motor-powered or manually actuable erection that rotates the at least one image sensor 26 about the longitudinal axis of the objective and/or the optical axis. In the event that two image sensors as in the present example are provided, both image sensors 26-1 and 26-2 are together rotated about an axis that is perpendicular to a stereo basis, wherein the axis is centered between the image sensors. In this way, the orientation (rotation orientation) of the detected image may be controlled.

The optical instrument 12 further comprises a shaft 40. At the proximal end of the shaft 40 that is facing away from the distal end, a handle housing 42 is formed. The optical instrument 12 is basically also arranged as a manually guidable instrument. Accordingly, the instrument 12 may be grasped and guided at the handle housing 42. Nevertheless, a fixed mounting to the stand (mounting arm) 14 is beneficial for a variety of applications.

The optical instrument 12 further comprises an interface 44 at the proximal end thereof that is, for instance, arranged as data interface or communication interface. Via the interface 44, image data may be transferred. The optical instrument 12 may further be supplied with control commands by the interface 44, which may be for instance generated by the control unit 22 and/or transferred by the external (part) image processing unit 20-2.

The image processing unit 20 that is illustrated in FIG. 1 as a distributed unit illustratively comprises a first processing module 46 and a second processing module 48. The first processing module 46 is associated with the instrument 12 and coupled with the image acquisition unit 18. The second processing module 48 is arranged as an external or separate processing module.

The observation device 10 further comprises a control unit 22 which will be described in more detail hereinafter. The control unit 22 is arranged to be mediately or directly coupled with the image acquisition unit 18, the image processing unit 20 and/or the image display unit 16.

The control unit 22 illustratively comprises an input module 50 which is, for instance, arranged as single-hand operable input module. The input module 50 comprises an actuation element 52, preferably a single-hand actuation element. The actuation element 52 is for instance puck-shaped, dome-shaped or button-shaped and/or disc-shaped. In certain embodiments, the actuation element 52 comprises a size allowing an operator to encompass the actuation element 52 with the hand, comparable to a computer mouse. Accordingly, the actuation element 52 of the input module 50 shown in FIG. 1 comprises a diameter of at least 30 mm (millimeter), preferably a diameter of at least 40 mm, further preferred a diameter of at least 50 mm. In this way, the actuation element 52 may also be grasped and actuated in a reliable and repetitive fashion when using gloves. For instance, the input module 50 comprises further actuation elements 54 arranged as buttons and such like in addition to the actuation element 52. In this way, additional functions may be provided.

In FIG. 1, lines that are designated by 56-1, 56-2, 56-3 and 56-4 illustrate that the components of the observation device 10 may generally communicate with one another may be in a direct or mediate way. It goes without saying that at least some of the lines 56-1, 56-2, 56-3 and 56-4 may be arranged at wireless connections. It may be further envisaged that the components of the observation device 10 are coupled with a common communication switch and that, as a result, a star-shaped topology is present. Other types, for instance bus systems and such like may be envisaged.

By way of example, the display 24 of the image display unit 16 illustrates organs of a patient. The image display unit 16 is arranged to illustrate a display image 60 that is based on a recorded image (not separately shown in FIG. 1) that is provided by the image acquisition unit 18. An overview image 62 may at least sectionally and at least temporarily overlay the display image 60, for instance similar to a picture-in-picture representation. The overview image 62 exemplarily elucidates a total area that may be detected by the image acquisition unit 18, wherein the display image 60, depending on the selected magnification, illustrates the total area or sub portions thereof. Accordingly, the overview image 62 facilitates orientation and/or navigation.

Figure 2:
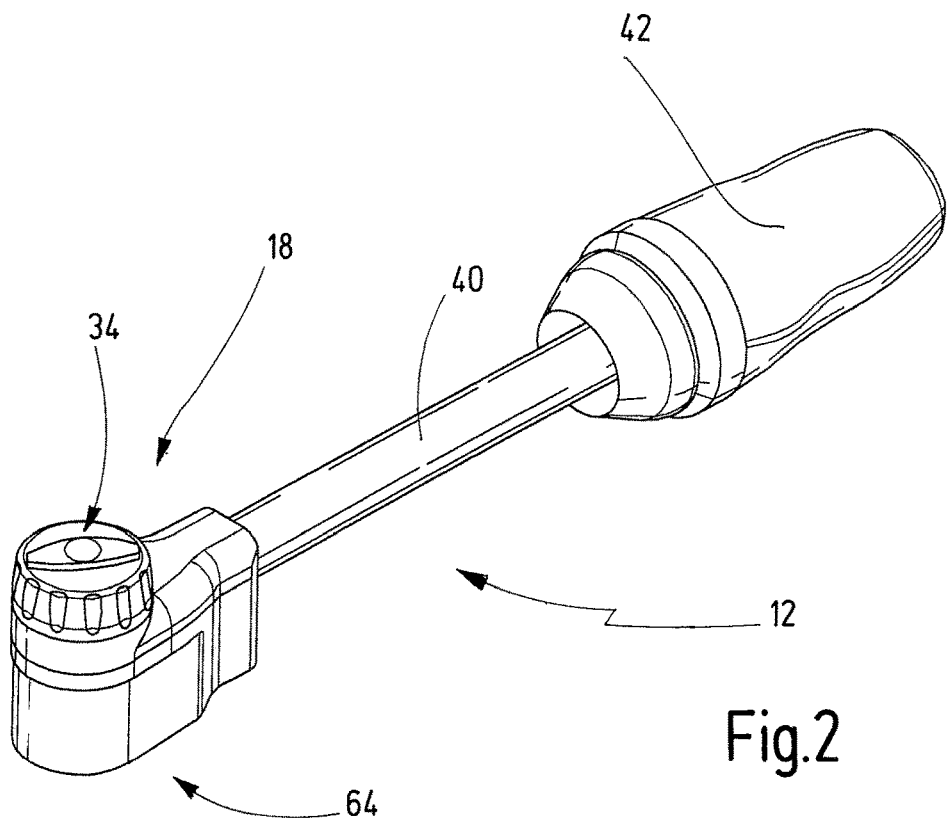
FIG. 2 is a perspective top view of an image acquisition unit that is arranged as an exoscope.
Figure 3:
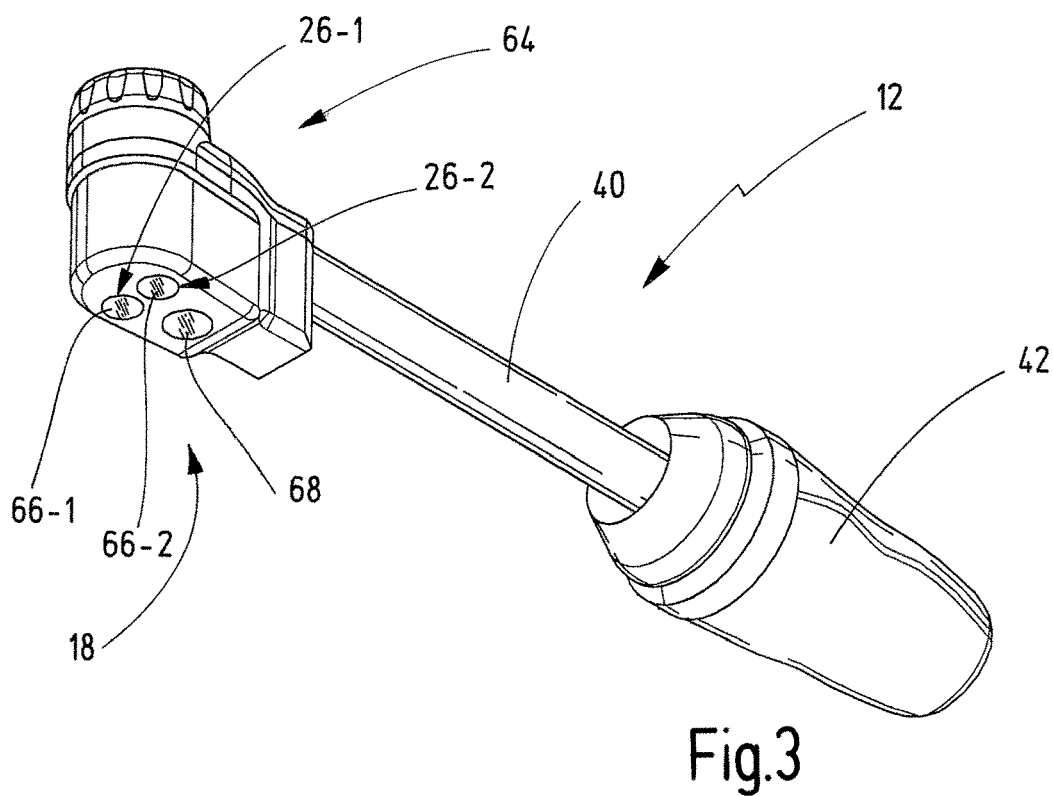
FIG. 3 is a further perspective view of the arrangement according to FIG. 2 in a different orientation.

With reference to FIGS. 2 and 3, an exemplary arrangement of an optical instrument 12 that is arranged as an exoscope is further elucidated. The optical instrument shown in FIGS. 2 and 3, in terms of the basic structure, corresponds basically to the optical instrument 12 according to FIG. 1.

The optical instrument 12 comprises a shaft 40, wherein a detector head 64 is arranged at the distal end thereof. The detector head 64 accommodates the image acquisition unit 18, at least parts thereof. At the proximal end of the shaft 40 that is facing away from the distal end, a handle housing 42 is formed with may accommodate further components of the optical instrument 12.

FIG. 3 illustrates that the optical instrument 12 is illustratively arranged as a stereoscopic instrument. Accordingly, the image acquisition unit 18 comprises in the region of the detector head 64 a first image sensor 26-1 and a second image sensor 26-2. Accordingly, two detector beam paths are present. First detector optics 66-1 is associated with a first detector beam path. Second detector optics 66-2 is associated with a second detector beam path. Further, illumination optics designated by 68, that is associated with the illumination unit 32, is shown in FIG. 3.

In an exemplary arrangement, the interface 44 (FIG. 1) of the optical instrument 12 is further configured to be coupled with a light guide and/or an external light source. Accordingly, the illumination unit 32 (refer to FIG. 1) does not necessarily have to be arranged as an active illumination. Rather, the illumination unit 32 may involve light guides extending between the proximal end and the distal end through the shaft 40 and leading to the illumination optics 68.

With reference to FIGS. 4, 5 and 6, several exemplary arrangements of input modules 50 that may be used at the control unit 22 will be elucidated hereinafter. It goes without saying that single aspects of one of the input modules 50 shown in FIGS. 4, 5 and 6 may also be incorporated in the other input modules.

A first arrangement of an input module 50 that is arranged for single-hand operation is shown in FIG. 4. The input module 50 comprises a main actuation element 52 that is for instance puck-shaped. The actuation element 52 is mounted to a basis 72 of the input module 50. Further, for instance, additional (secondary) actuation elements 54 are provided, for instance switches, buttons and such like. In FIG. 4 there is further a communication interface designated by 74 by means of which control signals may be provided which may be generated due to actuations of the actuation elements 52, 54.

In certain embodiments, input modules 50 in the context of the present disclosure are arranged as multi-axis input modules, for instance as four-axes input modules. An exemplary assignment of movement axes and/or actuation axes to the input module 50 is elucidated in FIG. 4. FIG. 5 illustrates an alternative assignment.

In FIG. 4, a translational direction is elucidated by a double arrow that is designated by 80. A rotation direction 82 that indicates a rotation about the axis of the translational direction 80 is illustrated by a curved double arrow designated by 82. Accordingly, the actuation element 52 may be translationally actuated (pulling and pushing). In addition, also a rotation actuation is enabled (turning).

Further actuation directions are identified in FIG. 4 by 84 and 86 which designate respective double arrows. The actuation directions 84, 86 may also be referred to as sliding directions. The sliding directions 84, 86 span a plane in which the actuation element 52 may be moved perpendicular to the translational direction 80. For instance, the actuation element 52 may be at least partially laterally deflected to generate a displacement signal.

By way of example, the axes of a coordinate system that is defined by the actuation directions 80, 84, 86 are designated by X (confer 86), Y (confer 84) and Z (confer 80). It goes without saying that this association primarily serves illustrative purposes. Modifications may be envisaged without further ado. The skilled person may easily apply necessary conceptual transformations. To enable the movements, using the degrees of freedom and/or the movement directions 80, 82, 84, 86, the actuation element 52 is mounted to the basis 72 in a fashion movable with respect to the basis 72, at least in defined limits. By way of example, optical sensors may be provided to detect the deflections and to assign the deflections to the respective axes.

In certain embodiments, input modules 50 presented in the context of this disclosure are arranged as input modules comprising haptic feedback. In this way, feedback may be provided to an operator that actuates the input module 50. By way of example, the haptic feedback is generated by a vibration motor or vibration generator 88 that is associated with the input module 50, for instance with the actuation element 52. The haptic feedback may for instance signal when limit values or extreme values are reached. In this way, it may be signaled to an operator that certain ranges or limit values may not be exceeded.

It may also be envisaged to provide a plurality of vibration generators 88 that are associated with at least some of the actuation directions and/or axes 80, 82, 84, 86. In this way, an even more sensitive and determined feedback may be provided.

FIG. 5 illustrates an alternative exemplary arrangement of an input module 50 for a control unit 22 that may be used at the observation device 10 according to FIG. 1. The input module 50 comprises a disc-shaped or cylindrical actuation element 90 which may be basically arranged similar to the actuation element 52. The actuation element 90 is supported at a basis 92 and connected with the basis 92 via a shaft 94. In terms of the movement axes and/or the actuation axes, the input module 50 elucidated with reference to FIG. 5 is modified with respect to the arrangement elucidated with respect to FIG. 4. As already illustrated in FIG. 4, a translational direction 80 and a rotation direction 82 is provided, wherein the rotation direction 82 indicates rotations about the translational direction 80. Instead of the sliding directions 84, 86 (confer FIG. 4), the arrangement according to FIG. 5 comprises swivel directions 98, 100 that represent respective deflections and/or pivot movements of the actuation element 90 about the X-axis and/or the Y-axis. Also by means of such an actuation movement, a respective signal may be generated that may represent a displacement in a two-dimensional space.

The actuation element 90 according to FIG. 5 is fixedly mounted to the basis 92. In other words, the actuation element 90 is not movably mounted to the basis 92. However, the actuation element 90 is sectionally deflectable and/or movable as for instance the shaft 94 is not arranged in an infinitely stiff fashion. In this way, defined deformations at the shaft 94 may be generated. The deformations may for instance involve compressions, stretching, deflections and/or twisting. Deformations of that kind may be detected by means of sensors 96, for instance by a plurality of respective sensors. By way of example, the sensors 96 may be arranged as strain gauges. Hence, even minimum deformations at the shaft 94 may be detected and assigned to the actuation directions 80, 82, 98, 100. The actuation element 90 according to FIG. 5 may also be coupled with an appropriate vibration generator 88 to provide haptic feedback.

The embodiment of the input module 50 elucidated with reference to FIG. 5 is integrally shaped as the actuation element 90 is fixedly coupled with the basis 92. In this way, the input module 50 is considerably robust. This may simplify cleaning procedures, for instance disinfection procedures and/or sterilization procedures. Hence, the input module 50 may easily be sterilized in an autoclave.

FIG. 6 elucidates a further arrangement of an input module 50 that is arranged for single-hand operation and that may be used at the control unit 22. The input module 50 comprises an actuation element 104 that is arranged basically similar to the actuation element already elucidated with reference to FIG. 4. The input module 50 further comprises a basis 108, wherein a hand rest 106 is formed at the basis 108. Further a plurality of additional actuation elements 54, for instance buttons, switches and such like is provided at the basis 108.

Figure 7:
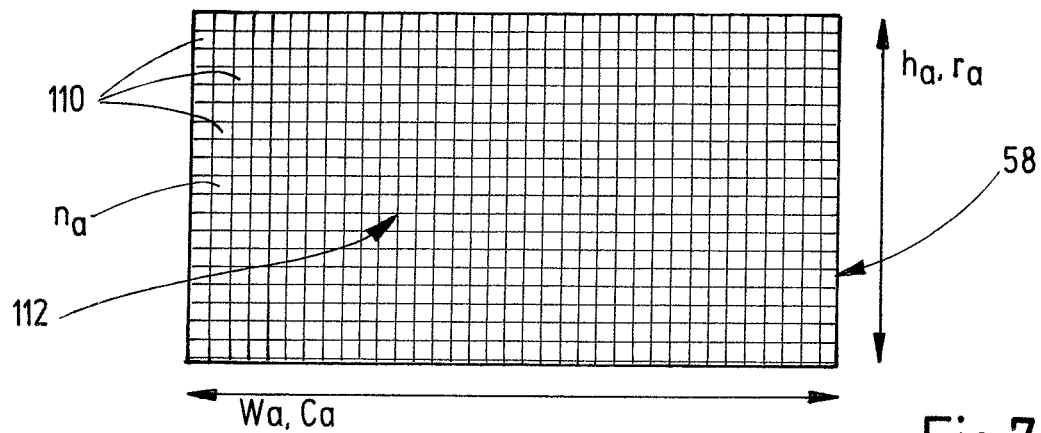
FIG. 7 is a schematic view of a recorded image.
Figure 8:
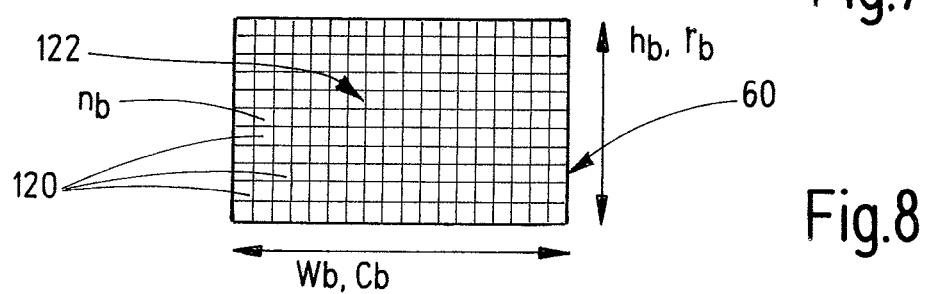
FIG. 8 is a schematic view of a display image.

With reference to FIG. 7 and FIG. 8, fundamental functions of the image acquisition unit 18 and the image display unit 16 will be explained in more details. FIG. 7 shows a recorded image 58 which can be detected and provided by the image acquisition unit 18. FIG. 8 shows a display image 60 which can be displayed by the image display unit 16. It is assumed hereinafter that the recorded images 58 and the display images 60 correspond to an image channel of a stereoscopic representation comprising two image channels, or two a (single) image channel of a non-stereoscopic representation. An extension to stereoscopic data may be envisaged without further ado.

The recorded image 58 according to FIG. 7 comprises a magnitude of pixels 110. A pixel quantity of the recorded image 58 will be referred to as $n_a$. Dimensions of the recorded image 58 are indicated in FIG. 7 by $w_a$ and $h_a$. The width of the recorded image 58 is designated by $w_a$ and involves a defined plurality of pixel columns $c_a$. The height of the recorded image 58 is designated by $h_a$ and comprises a defined number of pixel lines $r_a$.

The recorded image 58 covers a recording area 112. The recording area 112 basically corresponds to the area of the object plane 28 (confer FIG. 1) which is basically detectable with the image sensor 26 (however, confer the further explanations in connections with FIG. 12).

The display image 60 shown in FIG. 8 comprises a multitude of pixels 120. A pixel quantity of the display image 60 is $n_b$. Dimensions of the display image 60 are indicated in FIG. 8 by $w_b$ and $h_b$, wherein a width is designated by $w_b$ and a height is designated by $h_b$. The width $w_b$ comprises a defined number of pixel columns $c_b$. The height $h_b$ comprises a defined number of pixel lines $r_b$. The pixels 120 of the display image 60 define a display area 122.

In certain embodiments, the pixel quantities $n_a$ and $n_b$ are defined so that the pixel quantity $n_a$ of the recording area 112 is an integer multiple of the pixel quantity $n_b$ of the display area 122. By way of example, the display area 122 may be arranged as HD area (1280×720 pixels) or as Full HD area (1920×1080 pixels). Accordingly, the recording area 112 may comprise two times, three times, four times, six times or even eight times the number of pixels of the display area 122.

In certain embodiments, the aspect ratio ($c_a$:$r_a$) of the recording area 112 corresponds to the aspect ratio ($c_b$:$r_b$) of the display area 122.

The checkered illustration and/or square illustration used for indicating the recorded images 58 and/or the display images 60 elucidates corresponding pixel quantities $n_a$ and/or $n_b$. A comparison of FIG. 7 with FIG. 8 shows accordingly that the display area 122 that is displayable by the display image 60 corresponds merely to a subportion of the recording area 112 when the (detail) resolution or pixel density is maintained, i.e. when a contiguous area of the pixels 110 of the recording area 112 shall be illustrated in the display area 122. Accordingly, dimensions $w_b$, $h_b$ of the display areas 122 are, in terms of the object plane 28, smaller than the dimensions $w_a$, $h_a$ of the potentially available recording area 112.

Figure 9:
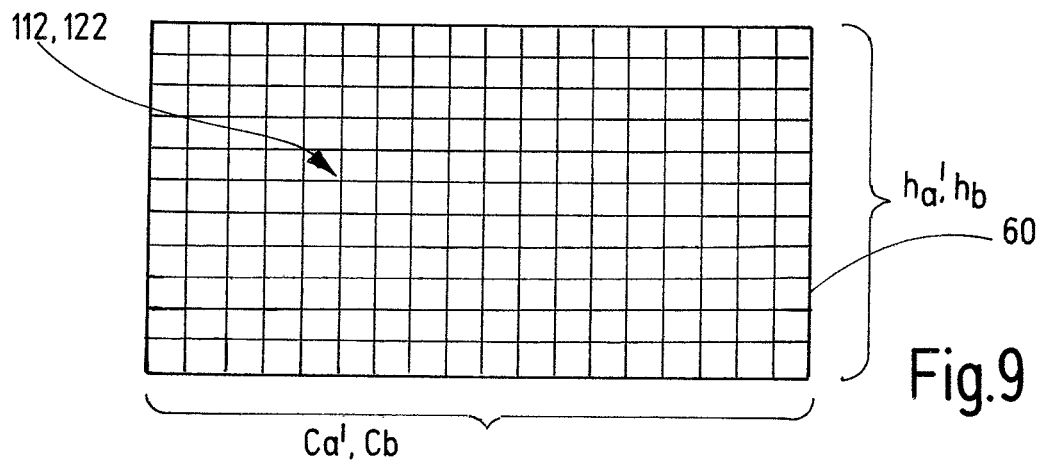
FIG. 9 is a schematic view of a display image that covers an area that corresponds to an area of a recorded image.

FIG. 9 elucidates a representation mode, wherein the display image 60 represents the entire recording area 112 of the recorded image 58. Accordingly, the display area 122 basically corresponds to the recording area 112. However, the pixel density is significantly smaller as only a limited number of pixels 120 is available in the display area 122. In other words, for instance, only each second or only each fourth of the pixels 110 of the recording area 112 is used for the representation in the display area 122. It goes without saying that also a respective average of neighboring pixels may be used to convert the pixel quantity $n_a$ of the recording area 112 to the pixel quantity $n_b$ of the display area 122. Accordingly, the representation in FIG. 9 is more coarsely screened than the representation in FIG. 7. In FIG. 9, $c_a'$ and $h_a'$ represent a number of columns and/or a number of lines that are derived from the original values $c_a$ and $h_a$ that correspond in this example to the values of $c_b$ and $h_b$, respectively.

Figure 10:
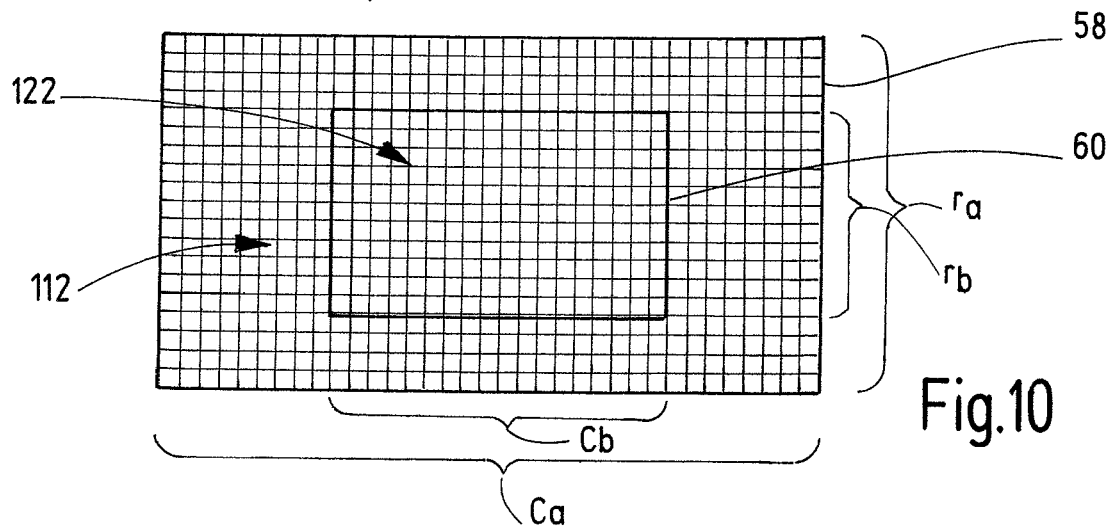
FIG. 10 is a schematic view of a display image that overlays a recorded image, for illustrative purposes, wherein a display image area covers a portion of the area of the recorded image.

FIG. 10 shows a representation mode, wherein the display image 60 is used for displaying merely a section of the recorded image 58. Compared to FIG. 9, the display image 60 of FIG. 10 does not show the entire recording area 112. In other words, the dimension of the display area 122 $c_b$, $r_b$ is smaller than the dimension $c_a$, $r_a$ of the recording area 112. In contrast to the representation according to FIG. 9, for the representation according to FIG. 10 a greater number of pixels or all the pixels in the selected section of the recording area 112 are illustrated in the display area 122. Depending on the selected magnification, for instance a 1:1 representation of at least a subset of the pixels 110 of the recording area 112 may be present in the display area 122. FIG. 9 shows an overview without magnification. FIG. 10 shows an intermediate magnification stage, wherein a section of the recorded image 58 is represented in the display image 60, wherein the section is selected in this magnification stage such that a contiguous subset of the pixels 110 of the recording area 112 forms the pixels 120 of the display area 122, refer in this context also to the illustration of FIG. 16, wherein the recorded image 58 and the display image 60 are separately shown for a better understanding.

Figure 11:
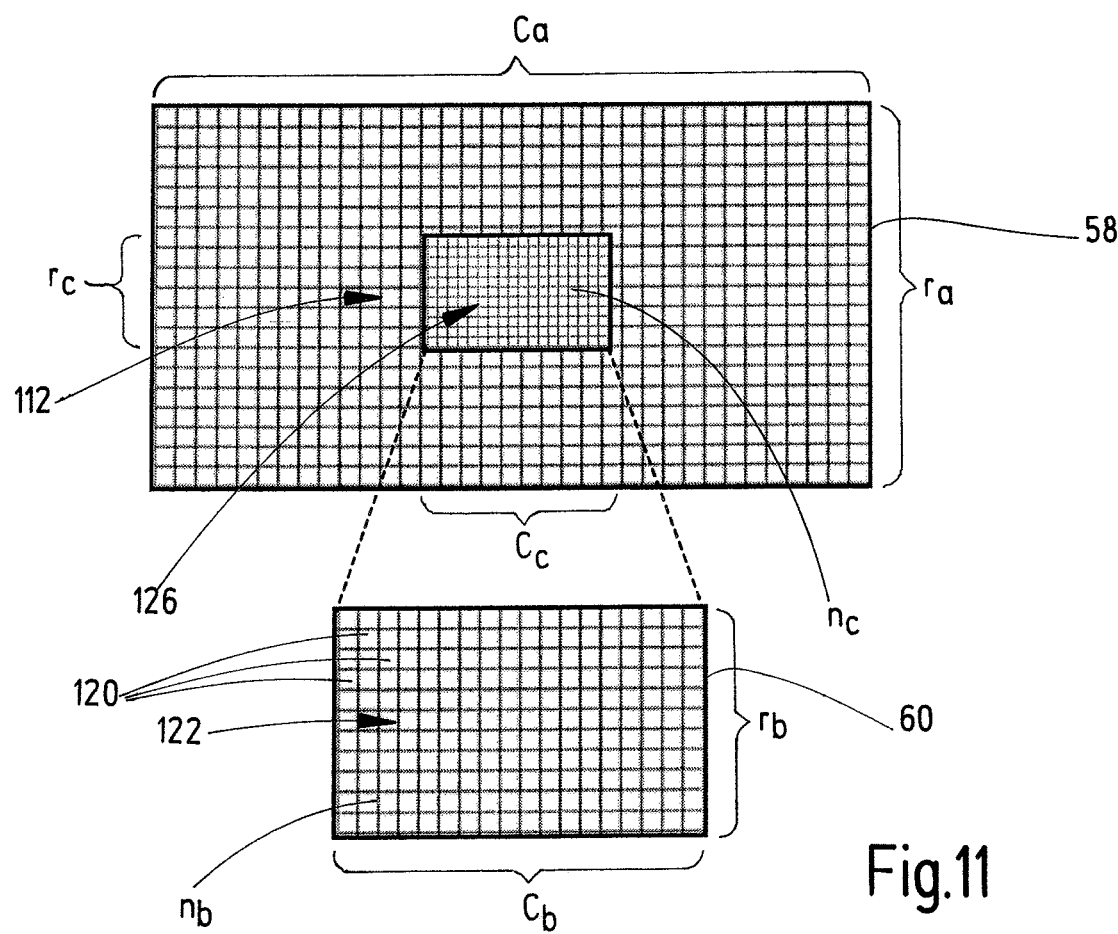
FIG. 11 is a further view in accordance with FIG. 10, wherein the display image covers a display area in the recording area of the recorded image having a pixel quantity that is smaller than the pixel quantity of the display area.

FIG. 11 elucidates a further magnification stage wherein an even smaller section 126 of the recording area 112 is represented in the display area 122. The section 126 extends in the recording area 112 over a defined number of pixels $n_c$ that is defined by a defined number of pixel columns $c_c$ and a defined number of pixel lines $r_c$. The pixel quantity $n_c$ of the section 126 is smaller than the pixel quantity $n_b$ that can be displayed in the display area 122 (refer to the illustration of the section 126 in FIG. 11, wherein for illustrative purposes the greater (display) pixel quantity $n_b$ overlays the smaller (sensor) pixel quantity $n_c$). In other words, a plurality of display pixels may correspond to a recording pixel. Accordingly, an interpolation and/or computational "upscaling" takes place to obtain the pixels 120 (pixel quantity $n_b$) of the display image 60 based on the limited pixel quantity $n_c$.

In this way, a greater magnification than for instance in the magnification mode according to FIG. 10 may be achieved, wherein the magnification is no longer loss-free. FIG. 10 shows a loss-free magnification. Depending on the ration between the number of pixels $n_a$ of the recording area 112 and the number of pixels $n_b$ of the display area 122, at least two loss-free representation stages and/or magnifications (refer to the overview representation in FIG. 9 and the magnification in FIG. 10) or even three, four, or even more loss-free magnification stages may be provided.

It goes without saying that also appropriate intermediate stages may be displayed, if desired. Respective interpolations may be applied. If a representation is desired that extends beyond the magnification shown in FIG. 10 (1:1-representation), interpolation procedures have to be applied. However, it has been observed that the resulting display images 60 are sufficiently detailed when the defined pixel quantity $n_b$, that is provided in the display area, is sufficiently large, for instance Full HD. A 1:1 representation (one-to-one representation) is provided when the pixel quantity in the selected section 122 in the recording area 112 corresponds exactly (or at least substantially) to the pixel quantity in the display area 122.

Figure 12:
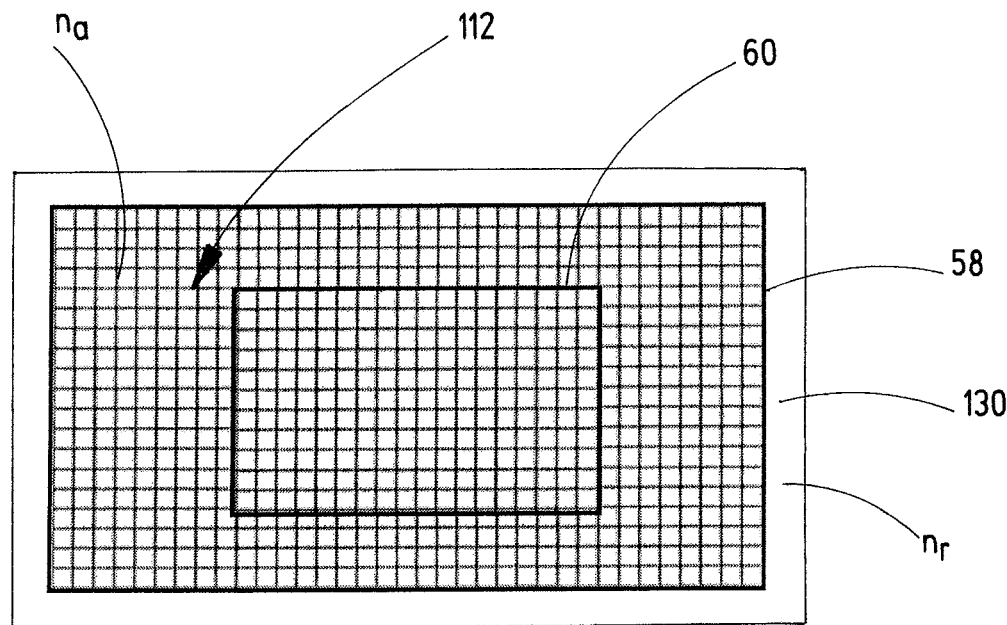
FIG. 12 is a further view of a recorded image, wherein an overall acquisition range is indicated which is greater than a recording area of the recorded image.

FIG. 12 elucidates a further exemplary arrangement, for instance relating to the image acquisition unit 18 and/or the at least one image sensor 26. By way of example, FIG. 12 elucidates a recorded image 58 and a selected display image 60 in the recorded image 58. The at least one image sensor 26 may basically be arranged to detect image data in an overall acquisition range 130 that is greater than the recording area 112 of the recorded image 58. For instance, a frame may be provided that overlaps the recording area 112. By way of example, the overall acquisition range 130 covers a raw data pixel quantity $n_r$ that is greater than the pixel quantity $n_a$ of the recording area 112.

The recording area 112 may be for instance selected in the overall acquisition range 130 such that an integer ratio between the pixel quantity $n_a$ of the recording area 112 and the pixel quantity $n_b$ of the display area 122 is ensured. A further feature may involve that the recording area 112 may be deliberately selected to be smaller than the overall acquisition range 130 to avoid disturbing effects that are often present in boundary regions of image sensors 26.

A further feature of the arrangement elucidated with reference to FIG. 12 may be present in regard of the stereoscopic image processing and image representation. The section of the overall acquisition range 130 that forms the recording area 112 of the image sensor 26 may be displaced, at least within narrow bounds. This may be beneficial for adjustment and/or fine tuning of the image acquisition unit 18. Further, when using two image sensors 26 that are capturing half images for the stereoscopic representation, a desired image distance between the half images may be adjusted by displacing the recording area 112 in the overall acquisition range 130. In this way, adjustment and fine tuning may be performed by means of software. In certain embodiments, in doing so, complex mechanical and/or optical adjustment tasks may be omitted.

Figure 13:
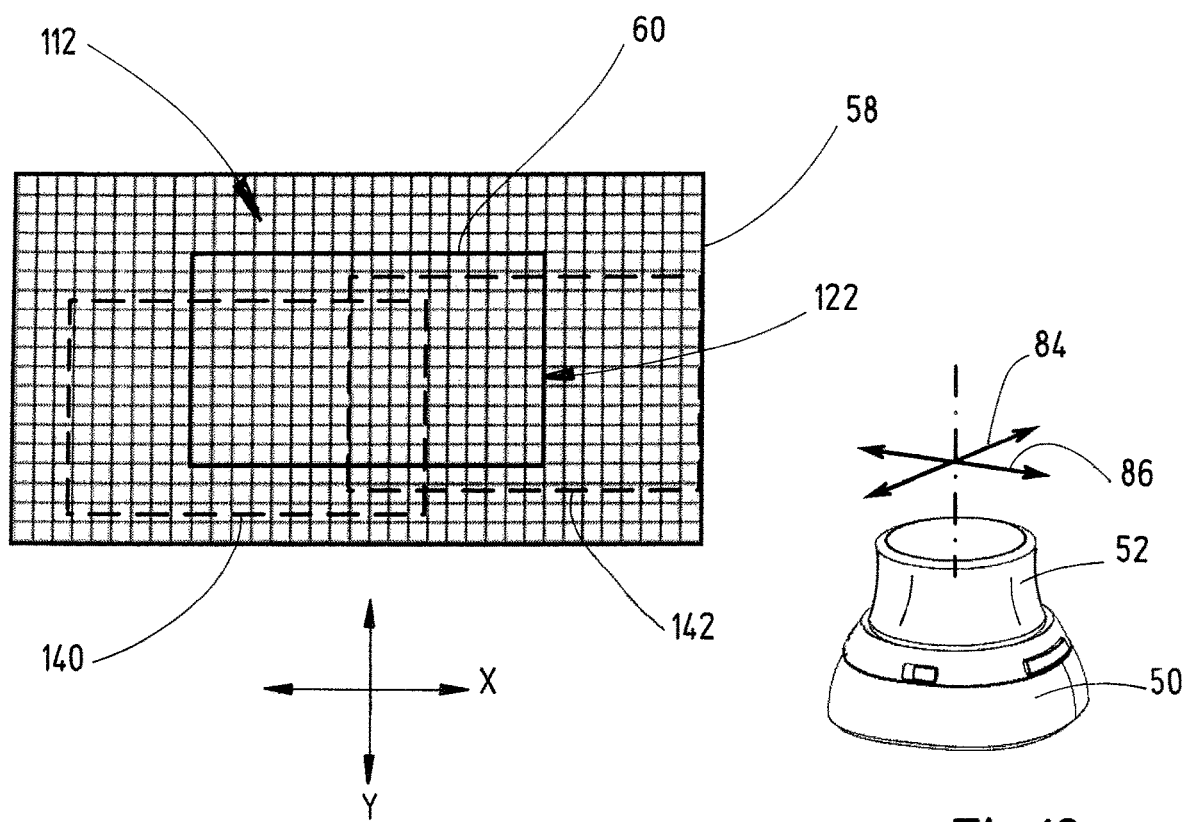
FIG. 13 is a schematic view of an input module and a display image which overlays a recorded image, for elucidating a position control.
Figure 14:
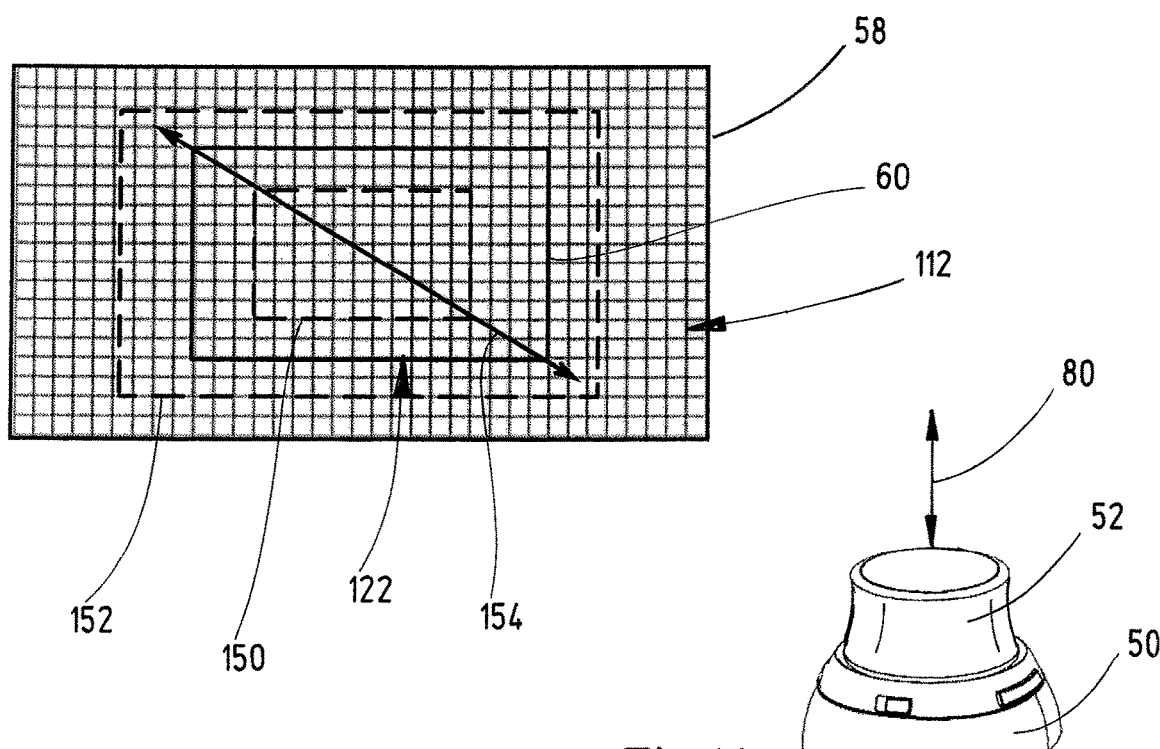
FIG. 14 is a further view that is similar to FIG. 13 for elucidating a zoom function.

With reference to FIGS. 13, 14 and 15, a beneficial assignment of actuation axes of the input module 50 for controlling image acquisition parameters and/or display parameters will be elucidated.

FIG. 13 shows a display image 60 that covers a display area 122 that is selected as a subset of the recording area 112 of the recorded image 58. The display area 122 may be displaced within the boundaries that are defined by the recording area 112, refer to arrows in FIG. 13 that are designated by X and Y. This sliding movement may be effected via the sliding directions 84, 86 of the input module 50. However, a respective displacement may also be controlled by the swivel directions 98, 100, refer to FIG. 5 in this context. Displaced display areas are designated in FIG. 13 by 140, 142.

FIG. 14 elucidates a zoom function, wherein areas of the recorded image 58 having a different size are selected to define the display area 122 based on which the display image 60 is derived.

A smaller section is designated by 150. The smaller section results in the generated display image in a magnification. A greater section is indicated by 152. The section 152 results in the represented display image in a reduction. A double arrow indicated by 154 elucidates the scaling of the display area 122 for generating different magnification stages.

The scaling may be achieved by an actuation of the input module 50 in the translational direction 80, i.e. by pushing or pulling the actuation element 52.

FIG. 15 elucidates a focus adjustment that may basically be provided in addition to the displacement according to FIG. 13 and to the magnification adjustment according to FIG. 14 by the input module 50. For instance, the image acquisition unit 18 comprises a focus drive and/or a focus adjustment. The view field 30 and/or the aperture angle of the view field 30 anyway are not easily adjustable in arrangements that do not comprise an optical zoom. However, the distance of a focus plane (also: focal plane) 160, 162, 164 having a sufficiently sharp representation may be modified by the image acquisition unit 18 to sharpen objects having a different distance to the image acquisition unit 18. In other words, an object that is in the foreground or an object that is in the background may be selectively sharpened. A respective displacement of the focus plane is indicated in 15 by a double arrow designated by 166. To this end, focus lenses in the optical instrument may be displaced. The displacement may be controlled by the input module 50.

By way of example, the sharpness adjustment may be effected by an action in the rotation direction 82. To this end, the actuation element 52 may be rotated about its longitudinal axis.

It is understood that also alternative arrangements may be envisaged, wherein for instance the magnification adjustment may be effected by rotating the actuation element 52 and the adjustment of the focus plane may be effected by pulling and/or pushing the actuation element 52.

The functions elucidated with reference to FIGS. 13, 14 and 15 each comprise a defined adjustment range. When limit values and/or extreme conditions are reached, haptic feedback may be provided at the input module 50 to signal this condition to the operator. By way of example, when displacing this section according to FIG. 13, approaching the boundary of the recording area 112 may be signaled. With the function shown in FIG. 14, for instance, haptic feedback may signal that the selected display area 122 corresponds to the recording area 112 and that consequently no smaller zoom stage is enabled. By contrast, it may be signaled that an extreme magnification (extremely small display area 122) is selected and that no further magnification is possible.

Similarly, also with the focus plane adjustment according to FIG. 15, feedback may be provided when a minimum distance or a maximum distance is achieved.

FIG. 16 elucidates a further exemplary function that may be provided by the observation device. As already described further above, FIG. 16 illustratively shows a recorded image 58 and a display image 60 that is formed based on a section of the recorded image 58 that defines a display area 122. The display image 60 covers the display area 122. According to at least some arrangements, it may be envisaged to display an overview image 62 in the display image 60, at least temporarily, that at least partially overlays the display area 122. This may be, for instance, implemented as picture-in-picture representation. In certain embodiments, the overview image 62 covers the entire recording area 112, even though in a coarsely screened representation. In this way, an optical orientation aid may be provided to the operator. Preferably, in the overview image 62 there is further indicated a section area 172 which is used as a position indicator. The section area 172 indicates the position of the selected display area 122 in the recording area 112 of the recorded image 58.

It may be envisaged to show the overview image 62 at least in situations when one of the functions illustrated in FIG. 13, 14 or 15 is used. If desired, the overview image 62 may also be displayed and faded out at the push of a button. The overview image 62 may be at least partially transparent to make an underlying area of the display area 122 at least partially visible.

The functions elucidated with reference to FIGS. 13, 14 and 15 illustrate that the input module 50 may be used to control image acquisition parameters and display parameters. This may take place simultaneously. By way of example, the current position of the focus plane is an image acquisition parameter. By way of example, a currently selected magnification stage or a current position of the selected image section (display area) in the potentially available recording area is a display parameter.

It goes without saying that the recorded image 58 that is shown in some of the figures illustrated herein is not necessarily visible. Rather, the recorded image 58 may be provided in the form of a respective data representation. By way of example, it may be envisaged that the recording area is constantly observed, at a selected frame rate, and, as a consequence, potentially available. Hence, the image acquisition unit 18 may provide a recording data stream that may be exploited, entirely or partially, to derive desired display images.

FIG. 17 is a schematic lateral view of a further embodiment of an observation device. In FIG. 17, an articulated holder 180 is shown. The holder 180 comprises, for example, an arm 182 to which a further arm 184 is mounted. The arms 182, 184 may also be referred to as columns or links. The holder 180 is merely partially shown in FIG. 17. Generally, the holder 180 may be referred to as stand or rack.

A carriage 186 is movably mounted at the arm 184. The arm 184 is movable mounted at the arm 182. Hence, the holder 180 may be provided with a positioning drive designated by reference numerals 190, 192 (indicating movement directions between the arms 182, 184, and the arm 184 and the carriage 186, respectively). At the carriage 186, an optical instrument 12 including an image acquisition unit 18 is releasably attached to the holder 180. Hence, the positioning drive 190, 192 may be operated to move the image acquisition unit 18.

In certain exemplary embodiments, the positioning drive 190, 192 may also be controlled by the input module 22, particularly the input module 50 thereof. In this way, an adjustment of a detection area of the image acquisition unit 18 is provided. As the input module 50 is, in at least some embodiments, a multi-axis input module, several movement axes of the positioning drive 190, 192 may be controlled simultaneously.

For releasably and accurately attaching the optical instrument 12 to the holder 180, a mounting interface 200 is provided. In certain exemplary embodiments, the mounting interface 200 involves a quick-lock mounting feature. The mounting interface 200 comprises a socket 202 that is provided with a recess 204. Further, a mounting bracket 206 is provided that comprises a mounting protrusion 208. In the exemplary embodiment illustrated in FIG. 17, the socket 202 is assigned to the carriage 186. Further, the mounting bracket 206 is arranged as a holder for the optical instrument 12. The mounting bracket 206 may be arranged as a clamp holder. Preferably, the mounting interface 200 comprises a locking feature that is actuated by a locking actuator 210. For attaching the optical instrument 12 to the holder 180, the mounting protrusion 208 is inserted into the recess 204, and locked therein, confer a respective mounting movement direction 212 in FIG. 17. The locking actuator 210 may control a locking feature, for example, a positive locking feature, a force-fit locking feature, etc. The locking actuator 210 is arranged to disengage and, if necessary, to engage the recess 204 and the mounting protrusion 208.

In the exemplary embodiment illustrated in FIG. 17, the input unit 22, particularly the input module 50 comprising the actuation element 52, is also attached to the holder 180. For instance, the input unit 22 is attached to an arm 218 that is mounted to the arm 182. In the alternative, the input unit 22 may also be attached to a separate holder or stand. In either case, a mounting interface 220 may be provided for releasably attaching the input unit 22 to the holder 180. In certain exemplary embodiments, the mounting interface 220 involves a quick-lock mounting feature. The mounting interface 220 comprises a socket 222 that is provided with a recess 224. Further, a mounting base 226 is provided that comprises a mounting protrusion 228. In the exemplary embodiment illustrated in FIG. 17, the socket 222 is arranged at the arm 218. The mounting base 226 is arranged at or forms part of the input module 50 of the input unit 22. Preferably, the mounting interface 220 comprises a locking feature that is actuated by a locking actuator 230. For attaching the optical instrument 12 to the holder 180, the mounting protrusion 228 is inserted into the recess 224, and locked therein, confer a respective mounting movement direction 232 in FIG. 17. The locking actuator 230 may control a locking feature, for example, a positive locking feature, a force-fit locking feature, etc. The locking actuator 230 is arranged to disengage and, if necessary, to engage the recess 224 and the mounting protrusion 228.

In FIG. 17, the mounting interfaces 200, 220 are shown in a partially detached state. The mounting interfaces 200, 220 may utilize the same mating elements (recess, protrusion, locking actuator) so that interchangeability is possible.

FIG. 18 is a schematic lateral view of an arrangement of an input module 22 comprising a single-hand input module 50 that is covered with a sterile cover 240. Hence, even in case the input module 50 is not arranged to be autoclaved or otherwise sterilized, on operation in medical applications is possible. The sterile cover 240 may be a disposable consumable.

The invention claimed is:

1. An observation device, comprising: an image acquisition unit comprising at least one image sensor, an image display unit that is arranged to display image data provided by the image acquisition unit, an image processing unit for image processing procedures, and a control unit comprising a multi-axis input module, wherein the image acquisition unit is configured to provide recorded images having a predefined recording pixel quantity, wherein the image display unit is configured to display display images having a predefined display pixel quantity, wherein the recording pixel quantity is equal to or greater than the display pixel quantity, wherein image pixels of the display pixel quantity are obtained from the recording pixel quantity, wherein, for providing views having different magnifications, subsets of the recording pixel quantity are selected to form the display pixel quantity, wherein the input module is arranged to control image acquisition parameters and display parameters, wherein the input module is arranged to be coupled with the image acquisition unit for controlling at least one image acquisition parameter, wherein an actuation element is arranged as four-axis actuation element, wherein an actuation of a first actuation axis defines a magnification and a size of an area of the display images in the recorded images that is associated with the magnification, wherein an actuation of a second actuation axis defines a focus setting, wherein an actuation of a third actuation axis effects a movement of the area that is covered by the display images in an area that is covered by the recorded images, in a first movement direction, and wherein an actuation of a fourth actuation axis effects a movement of the area that is covered by the display images in the area that is covered by the recorded images, in a second movement direction Y that is inclined with respect to the first movement direction.

2. The observation device as claimed in claim 1, wherein the observation device is arranged as a medical observation device, and wherein the at least one sensor is arranged to detect incident electromagnetic radiation in at least one of an UV range, a visible light range, and a IR range.

3. The observation device as claimed in claim 1, wherein the acquisition unit is a stereo-image acquisition unit comprising two image sensors.

4. The observation device as claimed in claim 1, wherein the input module is coupled with the image acquisition unit and the image processing unit to operate the image acquisition unit for modifying image acquisition parameters, and to operate the image processing unit for modifying display parameters, wherein the input module is preferably operable in at least a first operation mode and a second operation mode, wherein in the first operation mode a direct control of image acquisition parameters and display parameters is enabled, and wherein in the second operation mode a control of peripheral functions is enabled.

5. The observation device as claimed in claim 4, further comprising a positioning drive for the image acquisition unit, wherein the input module, in the second operation mode, is operable to control the positioning drive for positioning the image acquisition unit.

6. The observation device as claimed in claim 1, wherein the input module is arranged as a single-hand input module and provided with the actuation element that is manipulable by an operator and that provides a plurality of degrees of freedom of movement for inputs, particularly at least one translational direction, at least one rotation direction and at least two further degrees of freedom which are arranged as sliding directions or swivel directions.

7. The observation device as claimed in claim 6, wherein the actuation element is puck-shaped or knob-shaped, wherein the actuation element is coupled with sensors to detect a pull/push movement along a longitudinal axis of the actuation element, a rotation about the longitudinal axis, and sliding movements in a plane Y that is oriented perpendicular to the longitudinal axis, or swivel movements about pivot axes Y that are oriented perpendicular to the longitudinal axis.

8. The observation device as claimed in claim 1, wherein the actuation element is coupled with at least one sensor that is configured as a displacement transducer or a force transducer.

9. The observation device as claimed in claim 1, wherein the first actuation axis provides a translational direction, wherein the second actuation axis provides a rotation direction having an axis that is parallel to the translational direction, and wherein the third actuation axis and the fourth actuation axis respectively provide a sliding direction, for detecting a lateral deflection perpendicular to the translational direction, or a swivel direction, for detecting a lateral inclination about axes that are oriented perpendicular to the translational direction.

10. The observation device as claimed in claim 1, wherein the recording pixel quantity is an integer multiple of the display pixel quantity.

11. The observation device as claimed in claim 1, wherein the image processing unit is configured to provide the image display unit with a display pixel quantity that is displayed interpolation-free.

12. The observation device as claimed in claim 1, wherein the image acquisition unit is arranged to detect image data of a raw data pixel quantity that is greater than the recording pixel quantity, wherein the raw data pixel quantity corresponds to an overall acquisition range of the image sensor, and wherein the recording pixel quantity is selected as a section of the raw data pixel quantity.

13. The observation device as claimed in claim 1, wherein the control unit is configured to provide haptic feedback at the input module, particularly when achieving limit values or extreme values of parameter ranges that are controlled by the input module.

14. The observation device as claimed in claim 1, wherein the image processing unit is configured to generate overview images that represent an area that basically corresponds to the area that is covered by the recording pixel quantity, wherein the overview images comprise an overview pixel quantity that is selected to be smaller than the display pixel quantity, and wherein the overview images are displayed by the image display unit, at least temporarily parallel to the display images, wherein the overview images at least partially overlay the display images.

15. The observation device as claimed in claim 14, wherein the image display unit is configured to highlight a section area in the displayed overview images that indicates an area within the recording pixel quantity that is covered by the display pixel quantity, and wherein the section area is moved in the overview images when the area that is covered by the display pixel quantity is moved in the area that is covered by the recording pixel quantity by actuating the control unit.

16. The observation device as claimed in claim 1, wherein at least the image acquisition unit and the input module of the control unit are autoclavable.

17. The observation device as claimed in claim 1, wherein the control unit is provided with a mounting feature comprising a quick release coupling for releasably mounting the control unit to a holder or stand.

18. The observation device as claimed in claim 1, further comprising a sterile cover, wherein the control unit is arranged to be covered by the sterile cover, and wherein the input module is arranged to be actuated through the sterile cover.

19. A device for controlling image parameters comprising: a multi-axis input module that is arranged as a single-hand operable input module, a control unit of a medical observation device, the control unit including the multiaxis input module, wherein the control unit controls image acquisition parameters and display parameters, wherein the observation device comprises an image acquisition unit for providing recorded images having a predefined recording pixel quantity and an image display unit for displaying display images having a predefined display pixel quantity, wherein the input module comprises a plurality of actuation axes, wherein an actuation axis is arranged to be used to select a magnification mode and at least two actuation axes are arranged to be used for moving an area that corresponds to the display pixel quantity, in consideration of an actual magnification mode, in an area that corresponds to the recording pixel quantity wherein an actuation element is arranged as four-axis actuation element, wherein an actuation of the a first actuation axis defines a magnification and a size of an area of the display images in the recorded images that is associated with the magnification, wherein an actuation of a first actuation axis defines a magnification and a size of an area of the display images in the recorded images that is associated with the magnification, wherein an actuation of a second actuation axis defines a focus setting, wherein an actuation of a third actuation axis effects a movement of the area that is covered by the display images in an area that is covered by the recorded images, in a first movement direction, and wherein an actuation of a fourth actuation axis effects a movement of the area that is covered by the display images in the area that is covered by the recorded images, in a second movement direction Y that is inclined with respect to the first movement direction.

\* \* \* \* \*

UNITED STATES PATENT AND TRADEMARK OFFICE
CERTIFICATE OF CORRECTION

| | | |
|---|---|---|
| PATENT NO. | : 10,645,372 B2 | Page 1 of 1 |
| APPLICATION NO. | : 15/367600 | |
| DATED | : May 5, 2020 | |
| INVENTOR(S) | : Benedikt Köhler | |

It is certified that error appears in the above-identified patent and that said Letters Patent is hereby corrected as shown below:

On the Title Page

Column 1, (71) Applicant:
"Karl Storz GmbH & Co. KG, Tuttlingen (DE)"
Should read:
--Karl Storz SE & Co. KG, Tuttlingen (DE)--

Signed and Sealed this
Thirtieth Day of June, 2020

Andrei Iancu
*Director of the United States Patent and Trademark Office*